US011419481B2

(12) United States Patent
Inoue

(10) Patent No.: US 11,419,481 B2
(45) Date of Patent: Aug. 23, 2022

(54) MEDICAL SYSTEM AND OPERATION METHOD OF MEDICAL SYSTEM FOR CONTROLLING A DRIVER TO MOVE AN AREA DEFINED BY A PLURALITY OF POSITIONS OF A TREATMENT TOOL TO A PREDETERMINED REGION IN NEXT IMAGE CAPTURED

(71) Applicant: OLYMPUS CORPORATION, Tokyo (JP)

(72) Inventor: Shintaro Inoue, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 393 days.

(21) Appl. No.: 16/699,903

(22) Filed: Dec. 2, 2019

(65) Prior Publication Data
US 2020/0100649 A1 Apr. 2, 2020

Related U.S. Application Data

(63) Continuation of application No. PCT/JP2017/020841, filed on Jun. 5, 2017.

(51) Int. Cl.
*A61B 1/00* (2006.01)
*G06T 7/70* (2017.01)
*A61B 1/045* (2006.01)
*A61B 17/04* (2006.01)
(Continued)

(52) U.S. Cl.
CPC ...... *A61B 1/00009* (2013.01); *A61B 1/00133* (2013.01); *A61B 1/00149* (2013.01); *A61B 1/00188* (2013.01); *A61B 1/045* (2013.01); *A61B 17/0469* (2013.01); *A61B 17/29* (2013.01); *A61B 17/320016* (2013.01); *G06T 7/70* (2017.01); *A61B 2017/320004* (2013.01);
(Continued)

(58) Field of Classification Search
None
See application file for complete search history.

(56) References Cited

U.S. PATENT DOCUMENTS 7,841,980 B2 * 11/2010 Minosawa ............ A61B 17/34
600/117
2002/0156345 A1 * 10/2002 Eppler .................. A61B 90/50
600/102
(Continued)

FOREIGN PATENT DOCUMENTS

EP 2979610 A1 2/2016
JP H08-280695 A 10/1996
(Continued)

OTHER PUBLICATIONS

International Search Report dated Aug. 22, 2017 issued in PCT/JP2017/020841.

*Primary Examiner* — John P Leubecker
(74) *Attorney, Agent, or Firm* — Scully, Scott, Murphy & Presser, P.C.

(57) ABSTRACT

A medical system, having a treatment tool; an endoscope having an image sensor configured to capture an image; a driver configured to drive the endoscope; and a processor configured to control the driver, wherein the processor is configured to determine a locus of the treatment tool and control the driver for operating the endoscope according to the determined locus.

16 Claims, 13 Drawing Sheets

(51) Int. Cl.
*A61B 17/29* (2006.01)
*A61B 17/32* (2006.01)

(52) U.S. Cl.
CPC .............. *G06T 2207/10068* (2013.01); *G06T 2207/20104* (2013.01)

(56) References Cited

U.S. PATENT DOCUMENTS

| | | | |
|---|---|---|---|
| 2008/0108873 A1* | 5/2008 | Gattani | H04N 5/23296 382/128 |
| 2014/0005475 A1* | 1/2014 | Song | A61B 1/045 600/109 |
| 2014/0046341 A1* | 2/2014 | DiCarlo | H04N 5/2351 901/44 |
| 2016/0354166 A1* | 12/2016 | Popovic | A61B 1/00006 |
| 2017/0000574 A1* | 1/2017 | Itkowitz | A61B 1/00006 |
| 2017/0046842 A1* | 2/2017 | Yamaguchi | A61B 1/3132 |
| 2018/0317753 A1* | 11/2018 | Hou | A61B 1/04 |

FOREIGN PATENT DOCUMENTS

| | | |
|---|---|---|
| JP | H10-179512 A | 7/1998 |
| JP | 2012-147857 A | 8/2012 |
| WO | WO 2014/156218 A1 | 10/2014 |
| WO | WO 2015/149041 A1 | 10/2015 |

\* cited by examiner

MEDICAL SYSTEM AND OPERATION METHOD OF MEDICAL SYSTEM FOR CONTROLLING A DRIVER TO MOVE AN AREA DEFINED BY A PLURALITY OF POSITIONS OF A TREATMENT TOOL TO A PREDETERMINED REGION IN NEXT IMAGE CAPTURED

This application is a continuation application based on a PCT international Application No. PCT/JP2017/020841, filed on Jun. 5, 2017. The content of the PCT International Application is incorporated herein by reference.

FIELD OF THE INVENTION

The present invention relates to a medical system configured to perform treatment through a hole formed on the abdominal wall and the like, and an operation method of the medical system.

DESCRIPTION OF RELATED ART

Conventionally, in a laparoscopic surgery, a method is applied to form different holes (openings) on the abdominal wall and then insert a treatment tool and an endoscope therein respectively. The endoscope and the treatment tool inserted into the abdominal cavity are individually operated. In order to provide the most suitable visual field of the endoscope for an operator, a scopist operating the endoscope has to move the endoscope to the most suitable position.

In order to provide the most suitable visual field of the endoscope for the operator, the operator and the scopist have to communicate with each other efficiently. In a situation in which the most suitable visual field of the endoscope cannot be provided to the operator, the operator has to interrupt the treatment and wait for the scopist to finish the adjustment of the visual field of the endoscope.

In Japanese Unexamined Patent Application, First Publication. No. H8-280695, a surgical manipulator apparatus configured to automatically move an endoscope manipulator such that an image of the treatment tool is captured for adjusting the visual field of the endoscope during the exchange procedure of the treatment tools is disclosed. The operator can concentrate upon the exchange procedures of the treatment tools and the exchange procedures can be efficiently performed due to the wide-range visual field by the endoscope.

SUMMARY

According to a first aspect of the present invention, a medical system has a treatment tool, an endoscope having an image sensor configured to capture an image, a driver configured to drive the endoscope, and a processor configured to control the driver. The processor is configured to determine a locus of the treatment tool and control the driver for operating the endoscope according to the determined locus.

According to a second aspect of the present invention, in the medical system according to the first aspect, the processor may be configured to determine the locus of the treatment tool from the image.

According to a third aspect of the present invention, in the medical system according to the first aspect or the second aspect, the processor may be configured to operate the endoscope so as to make a center of the locus to be at a center of the image.

According to a fourth aspect of the present invention, in the medical system according to the first aspect or the second aspect, the processor may be configured to operate the endoscope such that an area proportion of a range determine by the locus with respect to the image is equal to a predetermined proportion value.

According to a fifth aspect of the present invention, in the medical system according to the first aspect or the second aspect, the processor may be configured to request an operator to select a partial region in the image, and the processor may be configured to operate the endoscope so as to make a visual field of the image to be focus on the partial region in a situation in which the locus is near to the partial region, and operate the endoscope so as to make the visual field of the image to be an overhead view of the partial region in a situation in which the locus is far from the partial region.

According to a sixth aspect of the present invention, in the medical system according to the first aspect or the second aspect, the processor may be configured to request an operator to select a partial region in the image, and the processor may be configured to operate the endoscope so as to capture an image of a distal end of the treatment tool in a situation in which the locus is near the partial region and stationary.

According to a seventh aspect of the present invention, in the medical system according to the first aspect or the second aspect, the processor may be configured to operate under at least one of operable operation modes having: an abrasion A mode in which the processor is configured to operate the endoscope so as to make a center of the locus to be at a center of the image; an abrasion B mode in which the processor is configured to operate the endoscope such that an area proportion of a range determine by the locus with respect to the image is equal to a predetermined proportion value; a suture mode in which the processor requests an operator to select a partial region in the image as a needle-applying region, wherein the processor is configured to operate the endoscope so as to make a visual field of the image to be focus on the needle-applying region, in a situation in which the locus is near to the needle-applying region, and wherein the processor is configured to operate the endoscope so as to make the visual field of the image to be an overhead view of the needle-applying region, in a situation in which the locus is far from the needle-applying region; and a dissection mode in which the processor requests the operator to select a partial region in the image as a dissection region, wherein the processor is configured to operate the endoscope so as to capture an image of a distal end of the treatment tool in a situation in which the locus is near the dissection region and stationary. The processor may be configured to operate under one operation mode which is selected among the operable operation modes.

According to an eighth aspect of the present invention, in the medical system according to the first aspect, the processor may be configured to acquire the locus of the treatment tool after determining a position of the treatment tool.

According to a ninth aspect of the present invention, an operation method of a medical system having a treatment tool, an endoscope having an image sensor configured to capture an image, a driver configured to drive the endoscope, and a processor configured to control the driver, has a detection processing of determining a locus of the treatment tool; and an operation processing of operating the endoscope according to the determined locus.

According to a tenth aspect of the present invention, in the operation method of a medical system according to the ninth aspect, the detection processing may be performed according to the image captured by the endoscope.

According to an eleventh aspect of the present invention, in the operation method of a medical system according to the tenth aspect, in the operation processing, the endoscope may be operated so as to make a center of the locus to be at a center of the image.

According to a twelfth aspect of the present invention, in the operation method of a medical system according to the tenth aspect, in the operation processing, the endoscope may be operated such that an area proportion of a range determine by the locus with respect to the image is equal to a predetermined proportion value.

According to a thirteenth aspect of the present invention, in the operation method of a medical system according to the tenth aspect, in the operation processing, a partial region in the image may be selected by an operator, the endoscope may be operated so as to make a visual field of the image to be focus on the partial region in a situation in which the locus is near to the partial region, and the endoscope may be operated so as to make the visual field of the image to be an overhead view of the partial region in a situation in which the locus is far from the partial region.

According to a fourteenth aspect of the present invention, in the operation method of a medical system according to the tenth aspect, in the operation processing, a partial region in the image may be selected by an operator, and the endoscope may be operated so as to capture an image of a distal end of the treatment tool in a situation in which the locus is near the partial region and stationary.

According to a fifteenth aspect of the present invention, in the operation method of a medical system according to the tenth aspect, in the operation processing, the endoscope may be operated under a selected operation mode among a plurality of operation modes including: an abrasion A mode in which the processor is configured to operate the endoscope so as to make a center of the locus to be at a center of the image; an abrasion B mode in which the processor is configured to operate the endoscope such that an area proportion of a range determine by the locus with respect to the image is equal to a predetermined proportion value; a suture mode in which the processor requests an operator to select a partial region in the image as a needle-applying region, wherein the processor is configured to operate the endoscope so as to make a visual field of the image to be focus on the needle-applying region, in a situation in which the locus is near to the needle-applying region, and wherein the processor is configured to operate the endoscope so as to make the visual field of the image to be an overhead view of the needle-applying region, in a situation in which the locus is far from the needle-applying region; and a dissection mode in which the processor requests the operator to select a partial region in the image as a dissection region, wherein the processor is configured to operate the endoscope so as to capture an image of a distal end of the treatment tool in a situation in which the locus is near the dissection region and stationary.

According to a sixteenth aspect of the present invention, in the operation method of a medical system according to the ninth aspect, in the detection processing, the locus of the treatment tool may be acquired after determining a position of the treatment tool.

DETAILED DESCRIPTION OF EMBODIMENTS

First Embodiment

A first embodiment of the present invention will be described by referring to FIG. 1 to FIG. 7. In order to make the figures easy to view, dimension of each configuration element is properly adjusted.

Figure 1:
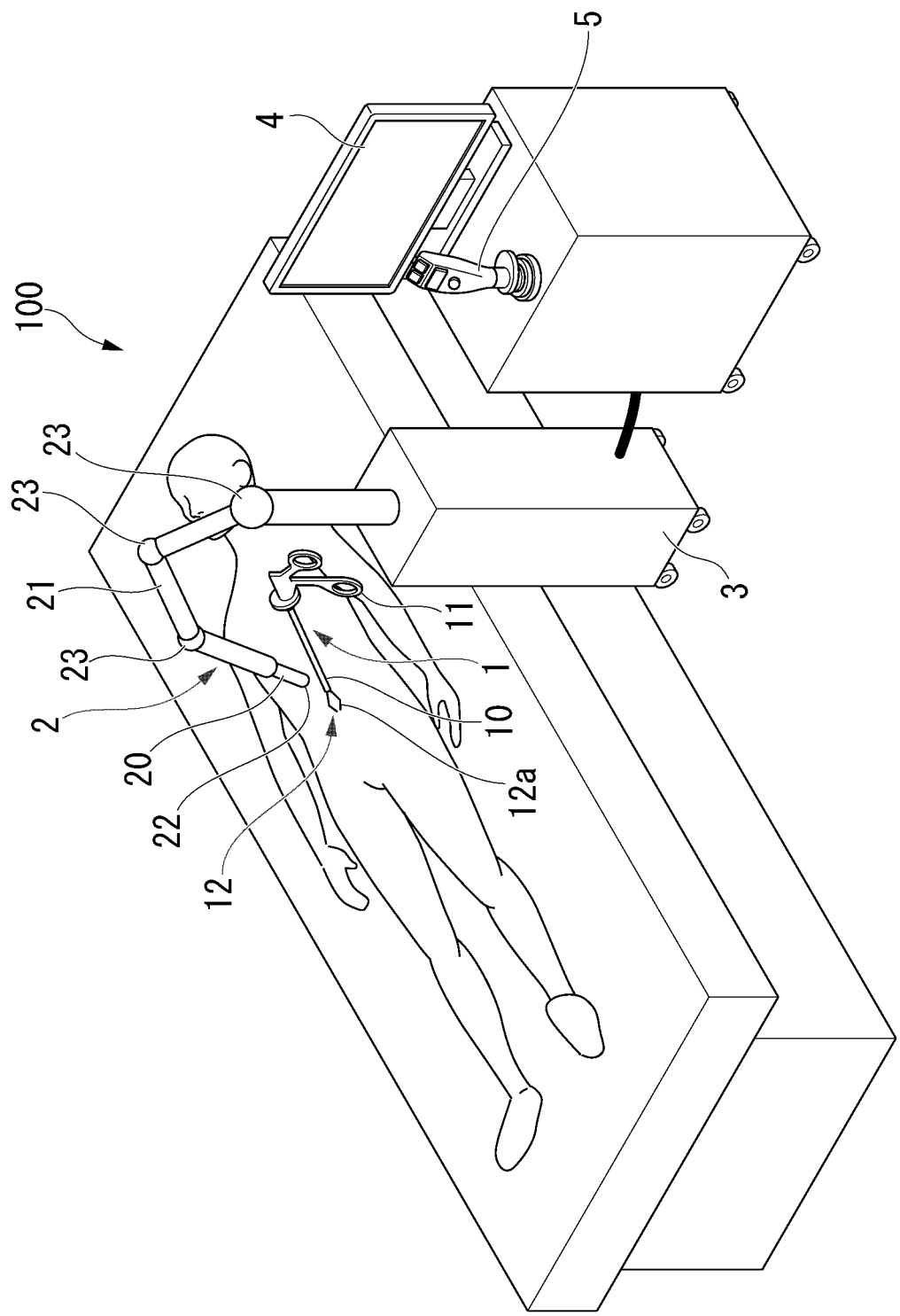
FIG. 1 is a view showing an overall configuration of a medical system according to a first embodiment of the present invention.

FIG. 1 is a view showing an overall configuration of a medical system 100 according to the present embodiment.

As shown in FIG. 1, the medical system 100 has a treatment tool 1, an endoscope 2, a control apparatus 3, a display 4, and an input device 5. The medical system 100 is a system configured to assist an operation of inserting the treatment tool 1 and the endoscope 2 from individual holes (openings) formed on the abdominal wall respectively during the laparoscopic surgery.

As shown in FIG. 1, the treatment tool 1 has an elongated insertion portion 10 being insertable into the abdominal cavity of a patient and an operation portion. 11 disposed at a proximal end portion of the insertion portion 10. The operator inserts the insertion portion 10 through a trocar penetrating the abdominal region of the patient so as to introduce the insertion portion 10 into the abdominal cavity. Due to the variation of the treatment and the situation of the lesion portion, the operator may introduce a plurality of treatment tools 1 into the abdominal cavity.

As shown in FIG. 1, the insertion portion 10 has a treatment portion (end effector) 12 at a distal end portion thereof which is configured to perform treatment with respect to the lesion portion of the patient. The treatment portion 12 according to the present embodiment is a grasping mechanism configured by a pair of grasping members 12a.

The operation portion 11 is a member configured to operate the pair of grasping members 12a. The operation portion 11 has a handle and the pair of grasping members 12a can be opened and closed by relatively moving the handle with respect to other parts of the operation portion 11. The operator can hold the operation portion 11 with one hand and operate the treatment portion 12.

Figure 2:
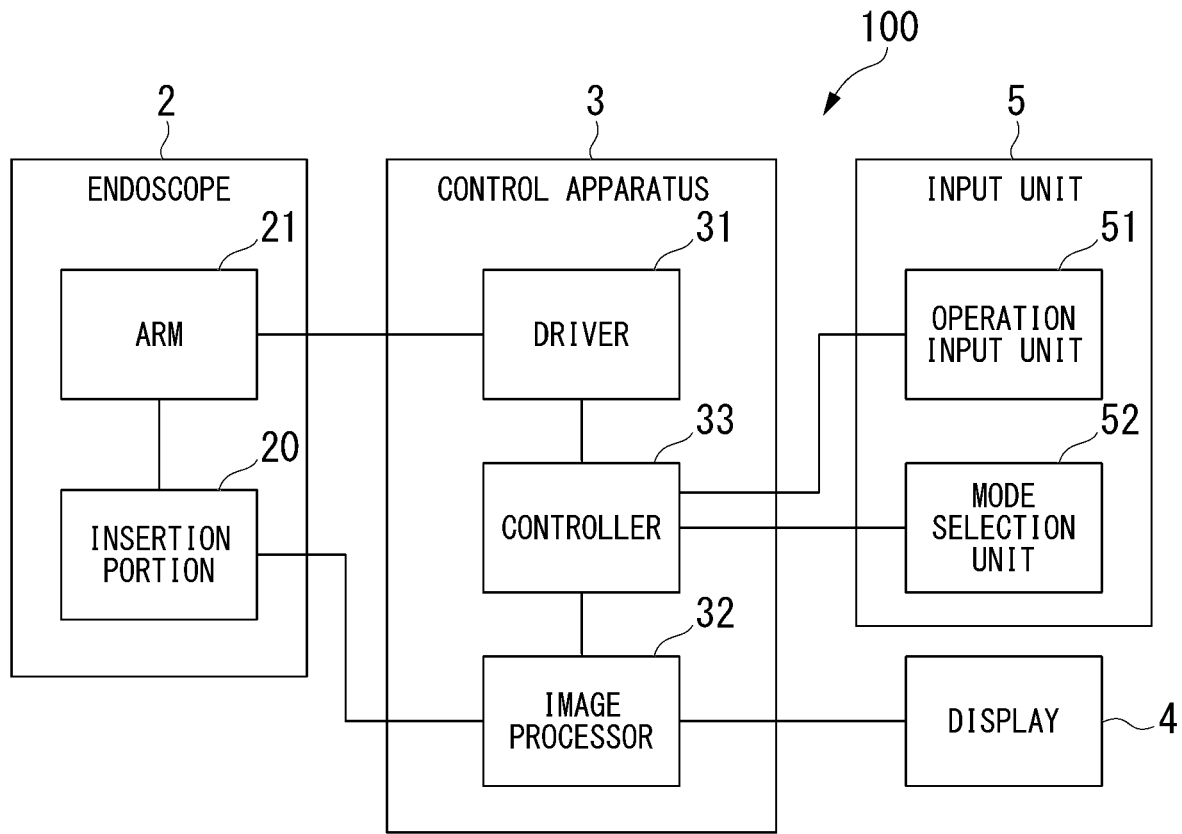
FIG. 2 is a view showing a hardware configuration of the medical system.

FIG. 2 is a view showing a hardware configuration of the medical system 100 excluding the treatment tool 1.

As shown in FIG. 1 and FIG. 2, the endoscope 2 has an elongated insertion portion 20 capable of being inserted into the abdominal cavity of the patient and an arm 21. The operator inserts the insertion portion 20 through the trocar penetrating the abdominal region of the patient to introduce the insertion portion 20 into the abdominal cavity.

At a distal end portion of the insertion portion 20, an image portion 22 having a lens and an image sensor configured to capture circumstances in the abdominal cavity of the patient is disposed. The insertion portion 20 introduced into the abdominal cavity is disposed at a position where the image portion 22 can capture an image of the lesion portion as the treatment target in the abdominal cavity. The image portion 22 may have functions such as optical zoom or electronic zoom.

The insertion portion may further have an active-bending portion that can bend actively. Due to the active-bending portion disposed at a part of the insertion portion. 20, it is possible to change directions of the lens and the image sensor of the image portion 22.

As shown in FIG. 2, the arm 21 is an electronically driven robot arm having at least one joint 23. A distal end of the arm 21 is connected with the proximal end portion of the insertion portion 20 of the endoscope, and the arm 21 is configured to be able to move the insertion portion 20.

The joint 23 is a portion bending around a rotation axis as a rotation center, wherein the joint 23 may be configured to actively bend due to a motor or the like, and the joint 23 may be configured to be passively bent due to the advancement and the retraction of the connected wire and the like. Inside the arm 21, control signal lines and wires configured to control the bending operation of the joint 23 is arranged. Inside the arm 21, control signal lines for controlling the image portion 22 and transmission signal lines for transmitting the images captured by the image portion 22 are also disposed.

As shown in FIG. 2, the control apparatus 3 has a driver (actuator) 31, an image-processing unit 32, and a control unit (controller) 33. The control apparatus 3 controls the arm 21 and the like due to the input from the input device 5. The control apparatus 3 transmits the images captured by the image portion 22 of the endoscope 2 to the display 4 as display images.

The driver 31 is configured to drive the joint 23 of the arm 21. In the situation in which the joint 23 is configured to actively bend, the driver 31 generates control signals for motors and the like to operate the joint 23. In the situation in which the joint 23 is configured to be passively bent, the driver 31 controls the advancement and the retraction of the wires for operating the joint 23. However, in each situation, the driver 31 is controlled by the control unit 33.

The image-processing unit 32 is connected with the transmission signal lines of the captured images that are captured by the image portion 22, and the image-processing unit 32 is configured to acquire the images via the transmission signal lines. The image-processing unit 32 generates the display images for display from the captured images. The image-processing unit 32 may have a memory configured to temporarily store the captured images, and the image-processing unit 32 may perform necessary image processing such as an image format transformation, a contrast adjustment and the like with respect to the stored images. The generated display images are transmitted to the display 4 at a predetermined transmission timing.

The image-processing unit 32 can generate the display images by replacing the captured images with images such as figures and characters generated by the control unit 33, or superimposing the images generated by the control unit 33 on the captured images. For example, the image-processing unit 32 can generate the display images by superimposing images of characters relating to warnings and operation assistance to the operator on the captured images.

The above-described images of the figures and characters may be generated by the image-processing unit 32 in accordance with the instructions of the control unit 33 rather than the control unit 33 itself.

The control unit 33 is configured to control the driver 31 and the image-processing unit 32 and the like according to input such as the operations of the input device 5 and the images acquired by the image-processing unit 32.

According to the present embodiment, the control unit 33 has two operations modes such as a manual mode and an abrasion A mode. The control unit 33 is configured to control the driver 31 and the image-processing unit 32 according to one selected operation mode between the two operation modes.

The manual mode is an operation mode in which the scopist operates the input device 5 to directly operate the joint 23 of the arm 21 of the endoscope 2 and the like.

The abrasion. A mode is an operation mode in which the joint 23 of the arm 21 of the endoscope 2 and the like are automatically operated by the control unit 33 so as to automatically adjust the visual field of the endoscope 2 when the lesion portion of the patient is abrased by the treatment portion 12.

The control unit 33 is configured by a device (computer) having hardware such as CPU (Central Processing Unit), memory and the like which can execute program. The function of the control unit 33 may be realized as function of software by making the control unit 33 to read and execute program for controlling CPU.

Also, at least part of the control unit 33 may be realized by exclusive logic circuits.

Furthermore, the same functions may be realized by connecting at least part of the hardware configuring the control unit 33 with communication lines.

Figure 3:
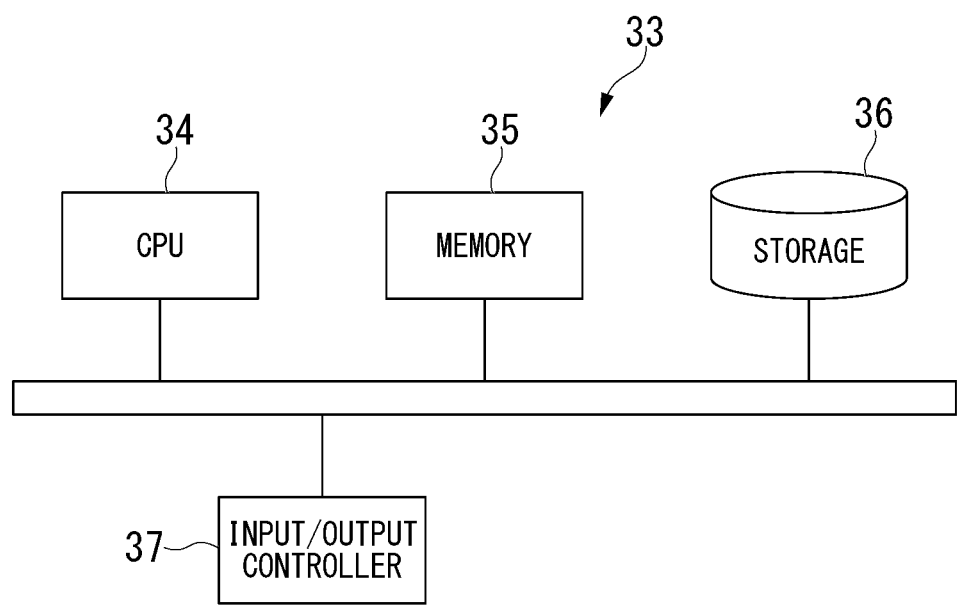
FIG. 3 is a view showing an overall configuration of a control unit of the medical system.
Figure 4:
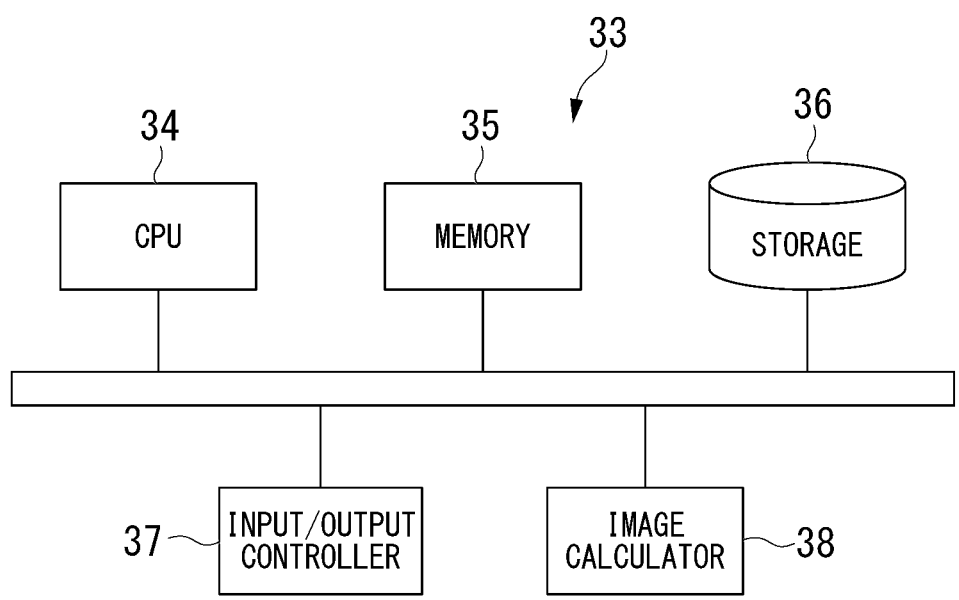
FIG. 4 is a view showing an overall configuration of the control unit of the medical system.

FIG. 3 and FIG. 4 are views showing an overall configuration of the control unit 33.

As shown in FIG. 3, the control unit 33 has a CPU 34, a memory 35 configured to be able to read program, a storage 36, and an input/output control unit 37. The program provided to the control unit 33 for controlling the operation of the controller 33 is read into the memory 35 and executed by the CPU 34.

The storage 36 is a non-volatile storage medium configured to store the program and necessary data. The storage 36 is configured by a ROM, a hard disk or the like. The program stored in the storage 36 is read into the memory 35 and executed by the CPU 34.

The input/output control unit 37 is configured to receive input data from the input device 5 and the image-processing unit 32 and transfer the input data to the internal module of the control unit 33 such as the CPU 34 and the like. Also, the input/output control unit 37 is configured to generate a control signal for the driver 31 and the image-processing unit 32 according to an instruction from the CPU 34 when the CPU 34 controls the driver 31 and the image-processing unit 32.

The control unit 33 may further have configurations for controlling the operation of the control apparatus 3 besides the CPU 34, the memory 35, the storage 36, and the input/output control unit 37 shown in FIG. 3. For example, as shown in FIG. 4, the control unit 33 may further have an image-calculation unit 38 configured to perform a part or all of a specific image processing and an image-recognition processing. The control unit 33 further has the image-calculation unit 38 so as to perform the specific image processing and the image-recognition rapidly.

The display 4 is a device for displaying the display images generated by the image-processing unit 32. The display 4 can be configured by the conventional display apparatus such as a LCD display and the like. The display 4 may be configured as a head mount display or a projector.

As shown in FIG. 2, the input device 5 has an operation input unit 51 and a mode-selection unit 52. The input device 5 is a device configured to input information necessary for the operation of the medical system 100.

The operation input unit 51 is a device configured to input operations of the joint 23 of the arm 21 of the endoscope 2. In the situation in which the image portion 22 has the zoom function, the operation input unit 51 can operate the zoom function thereof. In the situation in which the insertion portion 20 of the endoscope 2 has the active-bending portion, the operation input unit 51 can operate the active-bending portion to bend. The scopist operates the operation input unit 51 to operate the joint 23 of the arm 21 and the like.

As shown in FIG. 1, the operation input unit 51 may be configured by a joystick or a touch panel. The operation input unit 51 may be an operation input device having an arm with a shape similar to that of the arm 21. The display 4 such as the LCD display and the operation input unit 51 such as a touch panel may be integrally configured.

The operation content by operating the operation input unit 51 is transmitted to the control unit 33. The control unit 33 calculates the movement amount of the joint 23 of the arm 21 corresponding to the operation content. The control unit 33 controls the driver 31 so as to operate the joint 23 by the calculated movement amount.

In the situation in which the operation mode of the control unit 33 is the manual mode, the joint 23 and the like of the arm 21 of the endoscope 2 are directly operated by the operation of the operation input unit 51.

On the other hand, in the situation in which the operation mode of the control unit 33 is the abrasion A mode, the operation of the operation input unit 51 is deactivated by the control unit 33, and the joint 23 and the like of the arm 21 of the endoscope 2 cannot be operated. The joint 23 and the like of the arm 21 of the endoscope 2 are automatically operated.

The mode-selection unit 52 is a device configured to select an operation mode for the control unit 33 to operate between the two operation modes included in the control unit 33. The mode-selection unit 52 may be configured by a switch or by a touch panel. Also, the mode-selection unit 52 may be integrally configured with the operation input unit 51. The mode selection of the control unit 33 by the mode-selection unit 52 can be performed at any time.

Figure 5A:
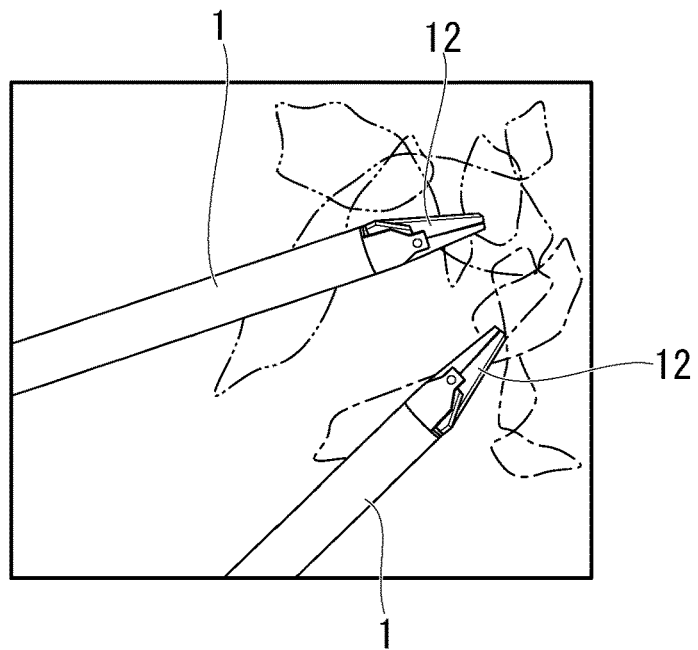
FIG. 5A is a captured image by an endoscope of the medical system.
Figure 5B:
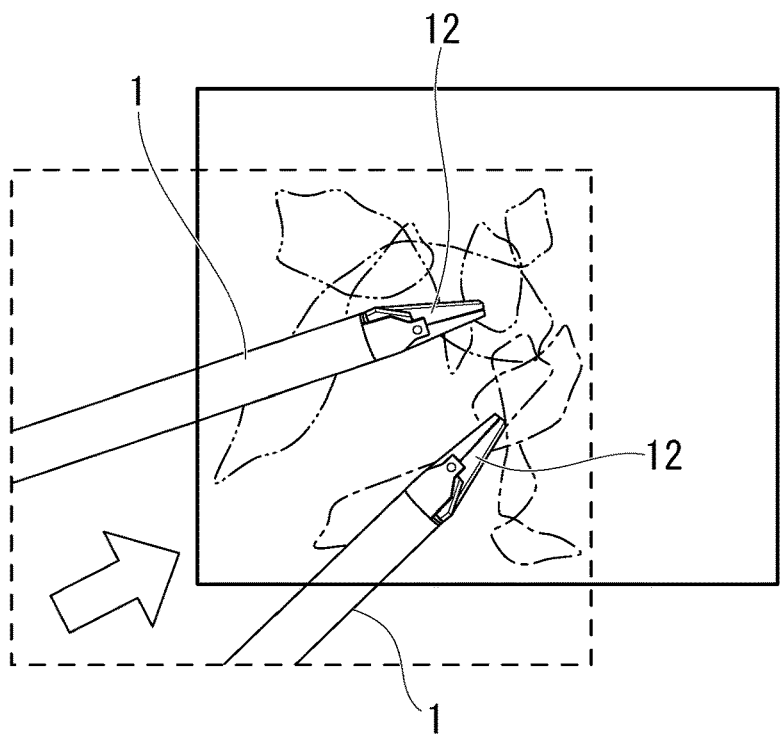
FIG. 5B is a captured image by the endoscope of the medical system.
Figure 6:
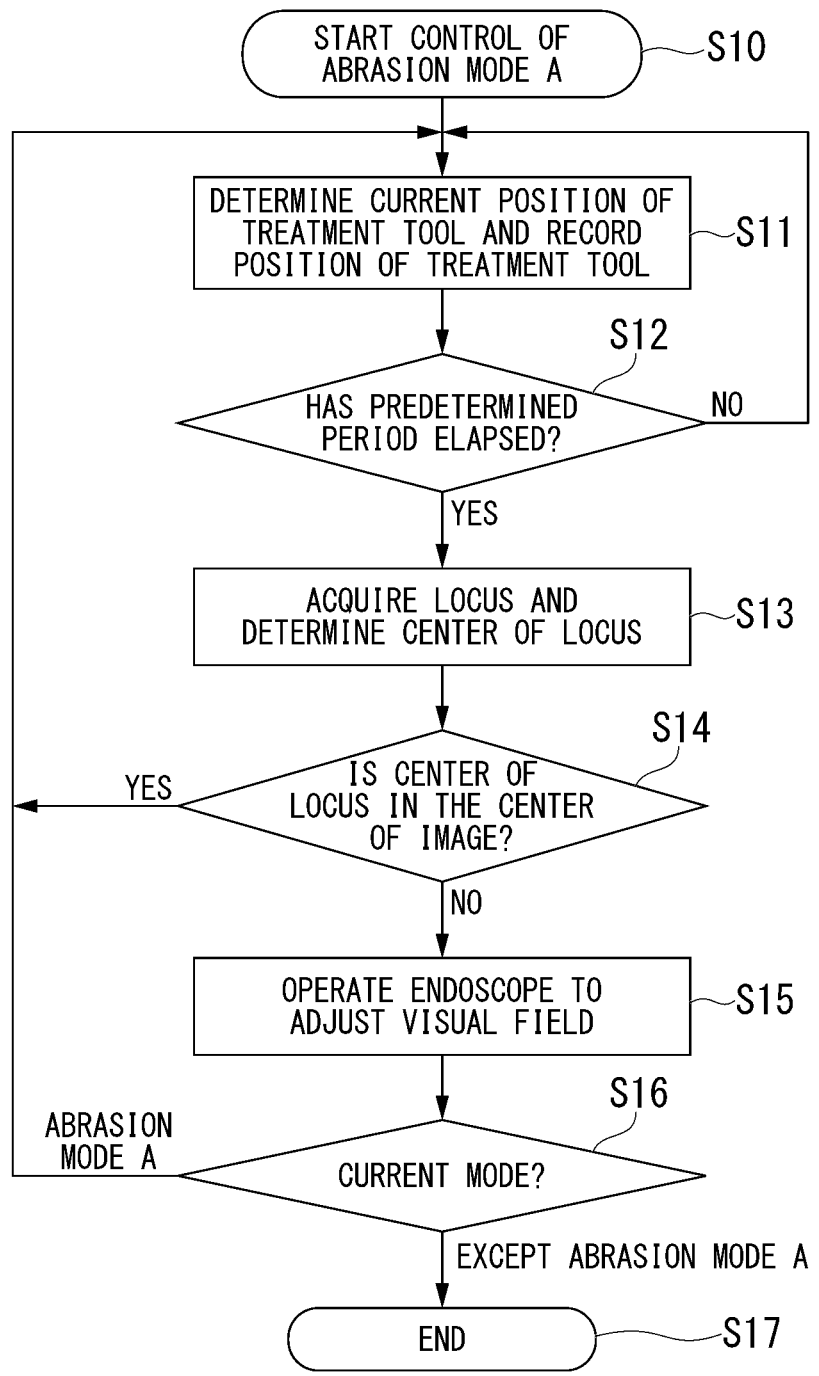
FIG. 6 is a flow chart showing a control flow of the control unit of the medical system in an abrasion A mode.

Next, using the laparoscopic surgery as an example, operations of the medical system 100 and an operation method of the medical system 100 will be described by referring to FIGS. 5A, 5B and FIG. 6. FIG. 5A and FIG. 5B are captured images by the endoscope 2 of the medical system 100. FIG. 6 is a control flow chart of the control unit 33 in the abrasion A mode.

The operator forms a plurality of holes (openings) for disposing the trocars on the abdominal region of the patient, and penetrates the trocars through the holes. Subsequently, the operator inserts the insertion portion 10 of the treatment tool 1 through the trocar penetrating the abdominal region of the patient to introduce the insertion portion 10 into the abdominal cavity.

Next, the scopist operates the mode-selection unit 52 to set the operation mode of the control unit 33 to the manual mode. The scopist operates the operation input unit 51 to operate the endoscope 2 so as to insert the insertion portion 20 of the endoscope 2 through the trocar penetrating the abdominal region of the patient to introduce the insertion portion 20 into the abdominal cavity. Furthermore, the scopist operates the operation input unit 51 to operate the endoscope 2 so as to capture the image of the treatment portion 12 by the image portion 22 to provide the most suitable visual field of the endoscope for the operator.

When the operator changes the variation of the treatment and the position of the lesion portion, the scopist operates the operation input unit 51 to operate the endoscope 2 so as to move the endoscope 2 to the most suitable position for the treatment and adjust the visual field of the endoscope 2 to be the most suitable visual field for the treatment.

In the situation in which the operator performs the abrasion treatment with respect to the lesion portion, the operator or the scopist operates the mode-selection unit 52 to change the operation mode of the control unit 33 to the abrasion. A mode, Hereinafter, the control flow chart of the control unit 33 in the abrasion A mode will be described by referring to FIG. 6.

As shown in FIG. 6, when the operation mode of the control unit 33 is changed to the abrasion A mode, the control unit 33 starts the control of the abrasion A mode (Step S10). The control unit 33 deactivates the operation input of the operation input unit 51. Accordingly, the scopist cannot operate the joint 23 of the arm 21 of the endoscope 2 by operating the operation input unit 51. Also, the control unit 33 activates a timer for measuring time to count the elapsed time.

Subsequently, the control unit 33 proceeds to Step S11.

In Step S11, as shown in FIG. 6, the control unit 33 determines the current position of the treatment tool 1 from the display image (detection processing). The control unit 33 performs a matching processing of the image data of the treatment portion 12 stored in the storage 36 in advance and the display image to determine the position of the treatment portion 12.

In the situation in which the control unit 33 has the image calculation unit 38 configured to perform the image matching processing rapidly, the matching processing can be executed rapidly. Also, it is possible to reduce the determination time for the position of the treatment tool 1 by applying a pattern or an optical marker suitable for the image matching processing on the treatment portion 12.

In the situation in which a plurality of treatment tools 1 are introduced into the abdominal cavity, the position of each treatment tool 1 is determined individually. In the situation in which the treatment portions 12 included in the plurality of treatment tools 1 have the same shapes with each other, for example, the control unit 33 can identify each treatment tool 1 by applying different patterns on the treatment portions 12 respectively.

In Step S11, the determined positions of the treatment tools 1 are recorded in the memory 35 for each treatment tool 1. The recorded positions, for example, are the two-dimensional coordinates in the display image. In the situation in which the image portion 22 has the function of measuring distance such as the stereo camera and the like, the recorded positions, for example, may be the relative three-dimensional coordinates with respect to the image portion 22.

Subsequently, the control unit 33 proceeds to Step S12.

In Step S12, as shown in FIG. 6, the control unit 33 refers to the timer used for measuring time to determine whether the elapsed time exceeds a predetermined period. In the situation in which the elapsed time exceeds the predetermined period, the control unit 33 proceeds to Step S13. In the situation in which the elapsed time does not exceed the predetermined period, the control unit 33 proceeds to Step S11. Here, the predetermined period may be set to about a few tens of seconds to a few minutes.

In Step S13, as shown in FIG. 6, the control unit 33 acquires the locus of the treatment tool 1 and calculates a center of the locus. In Step S13, the elapsed time has exceeded the predetermined period and the control unit 33 has executed the processing of Step S11 for several times. Accordingly, as shown in FIG. 5A, a plurality of positions are recorded in the memory 35 for each treatment tool 1. The control unit 33 acquires the plurality of positions for each treatment tool 1 as the locus of the treatment tool 1 from the memory 35. In FIG. 5A, the alternate long and short dashes line and the alternate long and two short dashed line indicate the locus of different treatment tools 1 respectively.

Subsequently, the control unit 33 calculates the center of the locus for each treatment tool 1. The center of the locus, for example, may be calculated from the average value of the coordinates. Also, the center of the locus may be acquired by calculating the centroid of the figure drawn by the locus and the centroid may be treated as the center. The center of the locus is considered to be the center of the region in which the treatment is performed.

In the situation in which there is a coordinate which is repeatedly recorded, the calculation for the center may be performed by increasing the weighting factor with respect to the coordinate. Since the coordinate which is repeatedly recorded can be considered to indicate the part at which the treatment is frequently performed in the region in which the treatment is currently performed, by increasing the weighting factor of the coordinate, the center of the locus can be calculated so as to approach the coordinate at which the center of the locus is repeatedly recorded.

Subsequently, the control unit 33 proceeds to Step S14.

In Step S14, as shown in FIG. 6, the control unit 33 determines whether the center of the locus is at the center of the display image. In the situation in which the center of the locus is not at the center of the display image, the control unit 33 proceeds to Step S15. In the situation in which the center of the locus is at the center of the display image, the control unit proceeds to Step S11. In the situation in which the processing branches in Step S11, the control unit 33 resets the timer for measuring time and returns the elapsed time to zero.

Here, the center of the display image, for example, is a region (center region) with the center of the display image as a center, and an area proportion of the region with respect to the area of the whole display image is 20% to 60%. The smaller the area proportion of the center region is (for example, 20% to 30%), Step S14, the higher the possibility that the processing branches in Step S15 is.

The area proportion of the center region can be adjusted due to the variation of the treatment and the preference of the operator.

In Step S15, as shown in FIG. 6, the control unit 33 operates the joint 23 of the arm 21 of the endoscope 2 to operate the endoscope 2 and adjust the visual field of the endoscope 2 (operation processing). As shown in FIG. 5B, the control unit. 33 operates the endoscope 2 such that the center of the locus of the treatment tool 1 acquired in Step S13 moves to the center of the display image. In the situation of using the plurality of treatment tool 1, the control unit 33 operates the endoscope 2 such that the center of the locus of any of the plurality of treatment tools 1, or the average coordinate of the center of the locus of the treatment tool 1 moves to the center of the display image. The smaller the area proportion of the center region is, the endoscope 2 is more positively operated.

When the control unit 33 moves the center of the locus of the treatment tool 1 to the center of the display image, the endoscope 2 may be operated such that part of the locus of the treatment tool 1 does not move to the outside of the display image. Since the range of the locus of the treatment tool 1 is considered to be the region where the treatment is currently performed, it is possible to prevent the region from moving to the outside of the display image.

In the adjusted visual field, as shown in FIG. 53, the center of the locus of the treatment tool 1 moves to the center of the display image such that the operator can achieve the most suitable visual field for the region in which the treatment is currently performed.

Subsequently, the control unit 33 proceeds to Step S16.

In Step S16, as shown in FIG. 6, the control unit 33 determines whether the operation mode selected by the mode-selection unit 52 is the abrasion A mode. In the situation in which the selected operation mode is the abrasion A mode, the control unit 33 proceeds to Step S11. In the situation in which the processing branches in Step S11, the control unit 33 resets the timer for measuring time and return the elapsed time to zero.

In the situation in which the selected operation mode is not the abrasion A mode, the control unit 33 proceeds to Step S17 and terminates the abrasion A mode.

The scopist is configured to operate the mode-selection unit 52 to change the operation mode of the control unit 33 to the manual mode so as to terminate the abrasion A mode by the control unit 33, and it is possible for the operator to directly operate the joint 23 of the arm 21 of the endoscope 2 by the operations of the operation input unit 51.

The problem shown below can be solved by operating the medical system 100 as described above.

In the situation in which the operator performs the abrasion treatment, there is a tendency that the locus of the treatment tool 1 concentrates in a specific region in which the lesion portion is positioned. Furthermore, as the abrasion treatment proceeds, there is a tendency that the position of the abrasion treatment moves little by little.

In this manner, in the abrasion treatment, since the region in which the treatment is currently performed, it is necessary to provide the visual field in which the center of the region is same with the center of the display image to the operator.

In the situation in which the center of the region in which the treatment is currently performed is not at the center (center region) of the display image, the visual field of the endoscope 2 is automatically adjusted to be the most suitable visual field for the abrasion treatment by the control unit 33 controlling the driver to operate the endoscope.

Effects of First Embodiment

According to the medical system according to the present embodiment, the operator can achieve the most suitable visual field for the current treatment by acquiring the locus of the treatment tool 1 that is considered to be the region for the current treatment and automatically operating the endoscope 2 so as to make the center of the locus to be same with the center of the display image.

According to the abrasion A mode of the medical system according to the present embodiment, the endoscope 2 is automatically operated in accordance with the movement of the center of the region in which the current treatment is performed such that the center of the region is same with the center of the display image. The repetitive operations of the endoscope 2 suitable for the abrasion treatment can be automated.

A method of making the endoscope to make the endoscope to perform a follow-up movement from time to time is considerable; however, according to such a method, the visual field in the display image moves frequently such that the operator cannot concentrate upon the observation with respect to the lesion portion.

According to the medical system 100 according to the present embodiment, the visual field adjustment is performed according to the locus of the treatment tool 1 acquired per the predetermined period such that it is possible to prevent the visual field in the display image from moving frequently. Also, the medical system 100 is configured to adjust the visual field according to the locus of the treatment tool 1 acquired in the predetermined period such that the most suitable visual field showing the whole region where the treatment is currently performed rather than the current position of the treatment tool. 1 can be provided.

Modification Example

Although the preferred First Embodiment of the present invention has been described above by referring to figures, the present invention is not limited to the embodiment. Additions, omissions, substitutions and other changes to the configuration elements disclosed in the present first embodiment and the modification example shown below are possible without departing from the spirit of the present invention.

For example, in the above-described embodiment, it is described that the locus of the treatment tool 1 is determined according to the image acquired by the image-processing unit 32, however, the determination method of the locus of the treatment tool 1 is not limited thereto. For example, a position of a position sensor disposed at the treatment portion 12 of the treatment tool 1 may be acquired and recorded as the locus of the treatment tool 1. Also, the portion for detecting the treatment tool 1 is not limited to the treatment portion 12 at the distal end of the treatment tool 1. The portion for detecting the treatment tool 1 may be a proximal end portion of the treatment tool 1 and the like.

Figure 7:
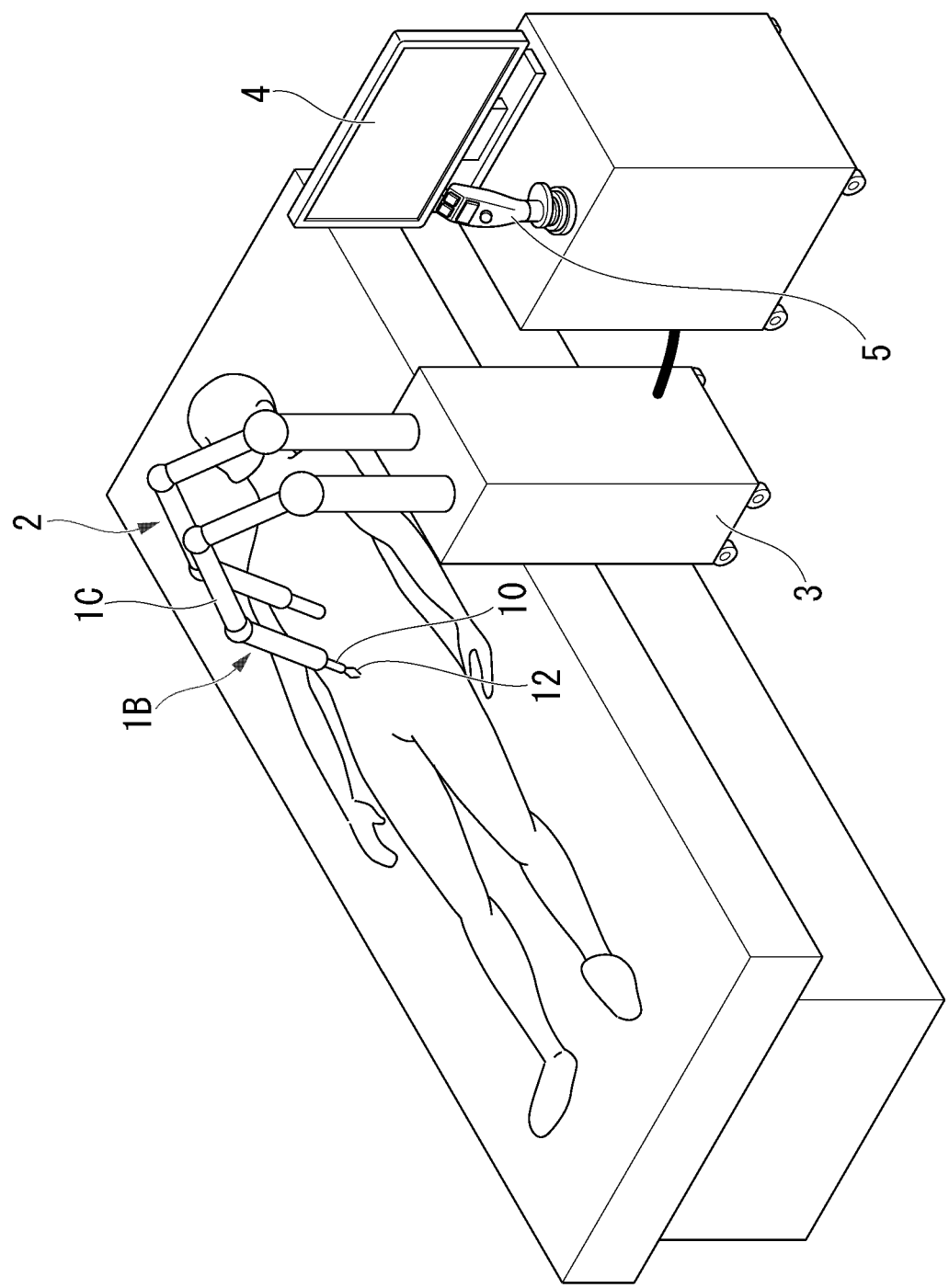
FIG. 7 is a view showing an overall configuration of a modification example of the medical system.

For example, in the present embodiment, it is described that the operator holds the treatment tool 1 in hand to perform the treatment. However, the embodiment of the treatment tool 1 is not limited thereto. For example, as shown in FIG. 7, as a treatment tool 1B as a modification example of the treatment tool 1, the insertion portion 10 may be a configuration driven by an arm 10. In this case, the locus of the treatment tool 1B can be calculated from the control information for driving the arm 10.

For example, in the present embodiment, it is described that the position of the treatment tool 1 determined in Step S11 is recorded. However, the embodiment of recording the position of the treatment tool 1 is not limited thereto. For example, the position of the treatment tool 1 may be recorded only in the situation in which the pair of grasping members 12a as the treatment portion 12 are closed. When the pair of grasping members 12a are closed, the position is considered to be the position where the treatment is actually performed. By recording the position, the region where the treatment is currently performed can be determined more accurately.

In the case in which the treatment portion is the high-frequency knife, the position of the treatment tool 1 may be recorded only in the situation when the current flows through the high-frequency knife.

For example, in the present embodiment, the program is stored in the storage 36, however, the accommodation method for the program is not limited thereto. For example, the program may be provided by a "computer-readable recording memory" such as a flash memory and the like. By connecting the flashing memory accommodating the program to a flash memory reader disposed at the control unit 33, the accommodated program can be read by the memory 35.

Also, the program may be provided from the computer accommodating the program in the storage device and the like to the control unit 33 by transmitting the program via a transmission medium or a transmission wave in the transmission medium. Here, the "transmission medium" for transmitting the program indicates a medium having the function of transmitting information such as a network as the internet (communication network) or communication channels (communication line) such as the telephone line.

The program may realize part of the above-described functions. Furthermore, the program described above may be a differential file (differential program) capable of realizing the above-described functions by being combined with the program that is already recorded in the computer.

In either situation, the program provided to the control unit 33 is read into the memory 35 and executed by the CPU 34.

Second Embodiment

A second embodiment of the present invention will be described by referring to FIG. 8A, FIG. 8B, and FIG. 9. In the present embodiment, the embodiment of determining the automatic operation of the endoscope 2 is different from that according to the first embodiment. In the following description, the common configurations which are already described will be assigned with same reference signs and the reductant descriptions will be omitted.

An overall configuration of a medical system 200 according to the present embodiment is same with that of the medical system 100 according to the first embodiment Comparing with the medical system 100, the medical system 200 is different in that the control unit 33 has an operation mode as an abrasion B mode instead of the abrasion A mode. Hereinafter, the control flow of the control unit 33 in the abrasion B mode will be described by referring to FIG. 8A, FIG. 8B, and FIG. 9. FIG. 8A and FIG. 8B are captured images by the endoscope 2 of the medical system 200. FIG. 9 is a flow chart showing a control flow of the control unit 33 in the abrasion B mode.

Figure 9:
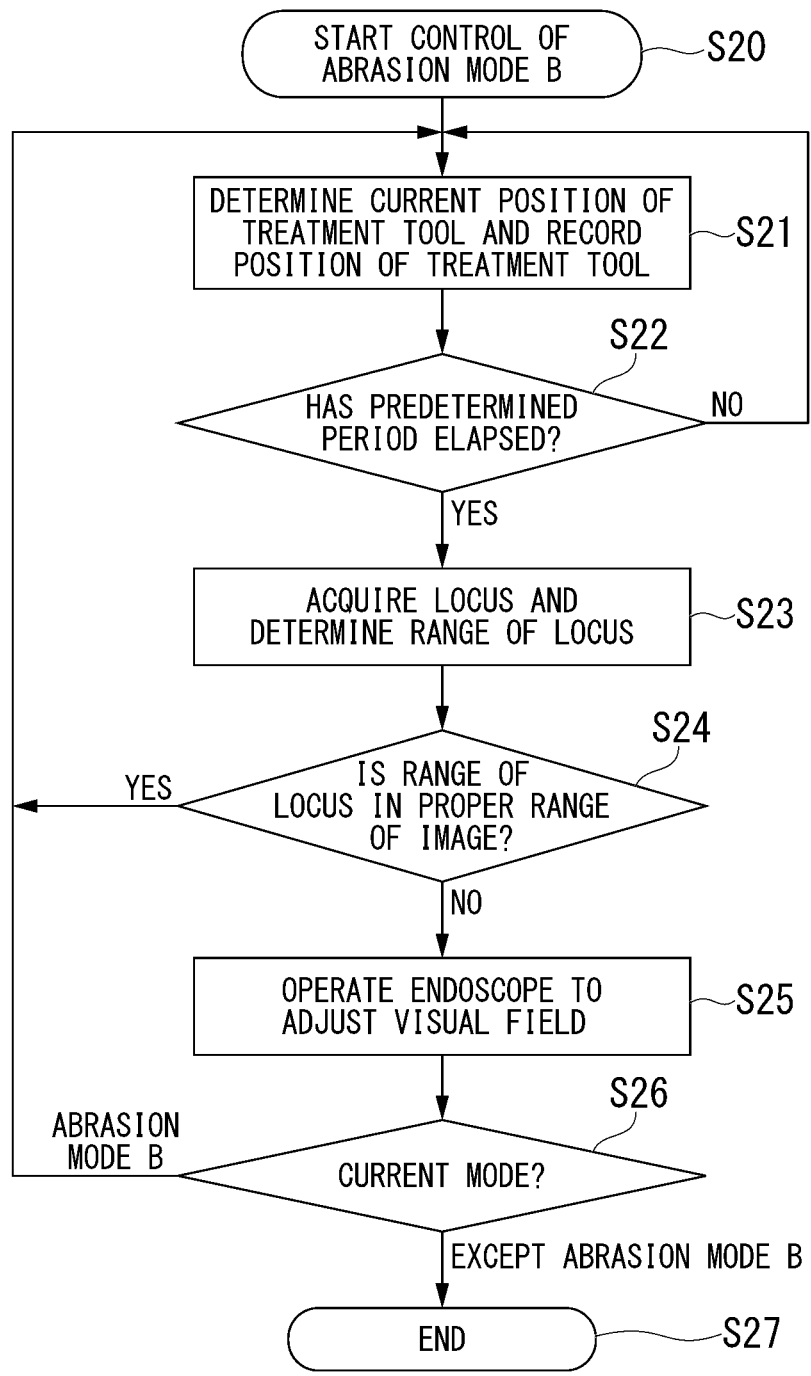
FIG. 9 is a flow chart showing a control flow of the control unit of the medical system in an abrasion B mode.

As shown in FIG. 9, when the operation mode of the control unit 33 is changed to the abrasion B mode, the control unit 33 starts the control of the abrasion B mode (Step S20). In Step S20, the control unit 33 performs the same processing with that in Step S10 according to the first embodiment. Subsequently, the control unit 33 proceeds to Step S21.

In Step S21, the control unit 33 performs the same processing with that in Step S11 according to the first embodiment (detection processing). Subsequently, the control unit 33 proceeds to Step S22.

In Step S22, the control unit 33 performs the same processing with that in Step S1.2 according to the first embodiment. In the situation in which the elapsed time exceeds the predetermined period, the control unit 33 proceeds to Step S23. In the situation in which the elapsed time does not exceed the predetermined period, the control unit 33 proceeds to Step S21 subsequently.

In Step S23, as shown in FIG. 9, the control unit 33 acquires the locus of the treatment tool 1 and calculates the range of the locus. In Step S23, the elapsed time exceeds the predetermined period and the control unit 33 has performed the processing of Step S21 for several times. Accordingly, as shown in FIG. 8A, a plurality of positions are recorded in the memory 35 for each treatment tool 1. The control unit 33 acquires the plurality of positions of the treatment tool 1 as the locus of the treatment tool 1 from the memory 35. In FIG. 8A, the alternate long and short dashes line and the alternate long and two short dashed line indicate the locus of different treatment tools 1 disposed at the left side and the right side, respectively.

A range of the locus is determined to have a predetermined shape which is selected from a group formed by a rectangle shape, an elliptic shape and the like, wherein the range of the locus having the locus of the treatment tool 1 inside thereof, and the range of the locus has a minimum area. As shown by the dotted lines in FIG. 8A, the range R of the locus has the rectangle shape having the locus of the treatment tool 1 inside and having the minimum area.

The shape of the range of the locus may not be the predetermined shape. The range of the locus may formed in a polygonal shape outside the locus of the treatment tool 1.

Subsequently, the control unit 33 proceeds to Step S24.

In Step S24, as shown in FIG. 9, the control unit 33 determines whether range of the locus is in an appropriate range in the display image. In a situation in which the range of the locus is not in the appropriate range in the display image, the control unit 33 proceeds to Step S25. In a situation in which the range of the locus is in the appropriate range in the display image, the control unit 33 proceeds to Step S21 subsequently. In the situation in which the processing branches in Step S21, the control unit 33 resets the timer for measuring time and returns the elapsed time to zero.

Here, the appropriate range in the display image is, for example, is a range with the center of the display image as a center, wherein an area proportion of the range with respect to the area of the whole display image is approximately 40% to 80%. The area proportion of the range of the locus can be adjusted due to the variation of the treatment and the preference of the operator.

Figure 8A:
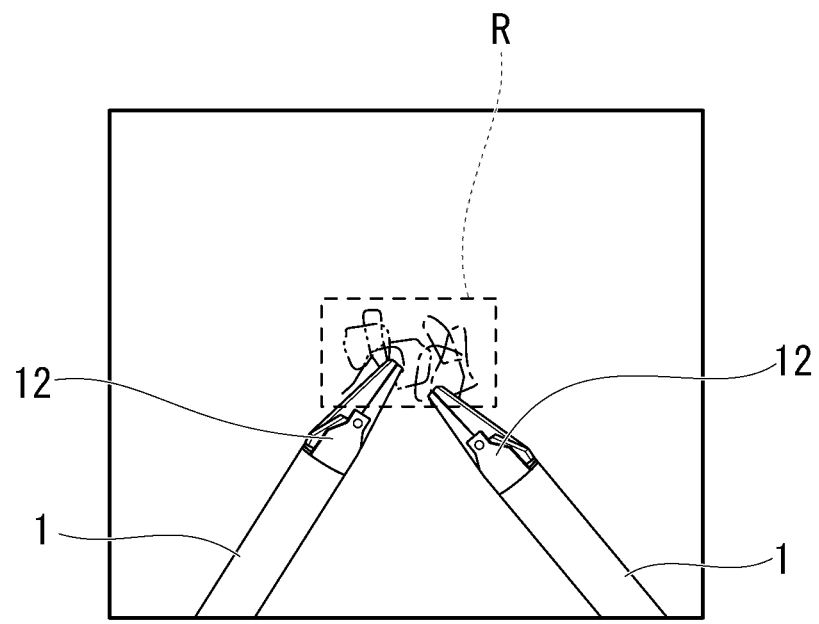
FIG. 8A is a captured image by an endoscope of: a medical system according to a second embodiment of the present invention.
Figure 8B:
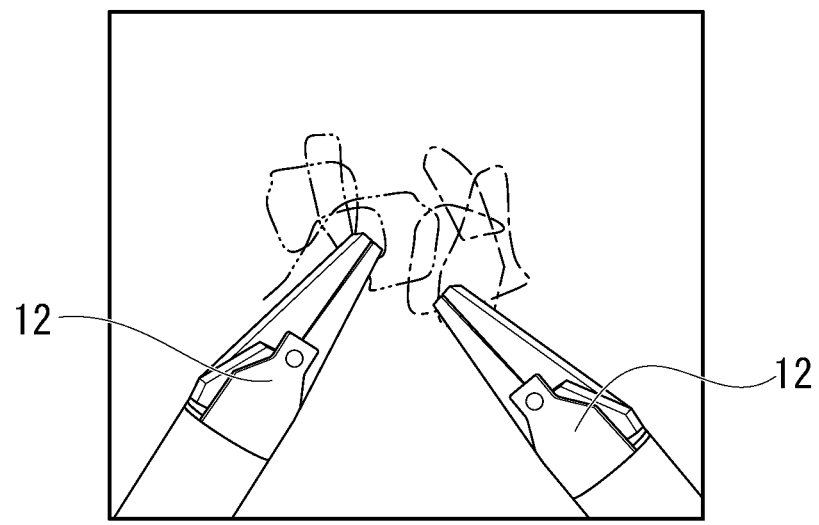
FIG. 8B is a captured image by the endoscope of the medical system according to the second embodiment.

For example, with regard to the range R of the locus of the treatment tool 1 shown in FIG. 8A, the area proportion with respect to the area of the whole display image is approximately 10% to 20%. In this case, the area proportion of the range of the locus with respect to the area of the whole display image is small and it is determined that the range of the locus of the treatment tool 1 is not in the appropriate range in the display image. In other words, it is determined that the area proportion of the range of the locus of the treatment tool 1 with respect to that of the display image is too small and it is not the most suitable visual field for the operator.

In another case in which the area proportion of the range of the locus of the treatment tool 1 with respect to the area of the whole display image is approximately 90%, it is determined that the area proportion of the range of the locus of the treatment tool 1 with respect to that of the display image is too large and it is also not the most suitable visual field for the operator.

In Step S25, as shown in FIG. 9, the control unit 33 operates the joints 23 of the arm 21 of the endoscope 2 to operate the endoscope 2 so as to adjust the visual field of the endoscope 2 (operation processing). As shown in FIG. 8B, the control unit 33 operates the endoscope 2 so as to make the range of the locus of the treatment 1 acquired in Step S23 to be the appropriate range in the display image. In the situation in which a plurality of treatment tools 1 are used, the control unit 33 operates the endoscope 2 to make the range of the locus of any treatment tool 1 or at least one range of the locus of the treatment tool 1 to be the appropriate range in the display image.

In the situation in which the image portion has the optical zoom or electronic zoom function, the visual field of the endoscope may be adjusted by operating the endoscope to activate the zoom function.

As shown in FIG. 83, in the adjusted visual field, the area proportion of the range of the locus of the treatment tool 1 with respect to the whole display image is approximately 40%, and the range of the locus of the treatment tool 1 is included in the appropriate range in the display image such that the operator can achieve the most suitable visual field for the region where the treatment is currently performed.

Subsequently, the control unit 33 proceeds to Step S26.

In Step S26, as shown in FIG. 9, the control unit 33 determines whether the operation mode selected by the mode-selection unit 52 is the abrasion B mode. In the situation in which the selected operation mode is the abrasion B mode, the control unit 33 proceeds to Step S21. In the situation in which the processing branches in Step S21, the control unit 33 resets the timer for measuring time and returns the elapsed time to zero.

In the situation in which the selected operation mode is not the abrasion B mode, the control unit 33 proceeds to Step S27 subsequently and the control of the abrasion B mode is terminated.

The scopist operates the mode-selection unit 52 to change the operation mode of the control unit 33 to the manual mode to terminate the control of the abrasion B mode by the control unit 33, thus, the joints 23 of the arm 21 of the endoscope can be directly operated by the operation from the operation input unit 51.

By operating the medical system 200 in such manner, the problems shown below are solved.

In the case in which the operator actually performs the abrasion treatment with respect to the target lesion portion, the operator performs the treatment in the proximity range with respect to the lesion portion. In this situation, the operation desires the visual field of the endoscope 2 in the proximity of the lesion portion.

On the other hand, in the situation of pulling the target lesion portion and securing a surgical space for the abrasion treatment, the operator performs the treatment in a wide range including the lesion portion. In this situation, the operator generally desires the visual field of the endoscope 2 to include the lesion portion in the overhead view.

During the abrasion treatment, even if the center position of the treatment is the same, since the range of the region where the treatment is currently performed changes, it is necessary to alternately provide the visual filed in the proximity of the lesion portion and the visual field in the overhead view to the operator.

In the situation in which the range of the region where the treatment is currently performed is not the most suitable range in the display image, the control unit 33 controls the driver 31 to operate the endoscope 2 such that the visual field of the endoscope 2 is automatically adjusted to the most suitable visual field for the abrasion treatment.

Effects of Second Embodiment

According to the medical system 200 according to the present embodiment, the operator can achieve the most suitable visual field for the current treatment by acquiring the locus of the treatment tool 1 considered to be the region where the treatment is currently performed and automatically operating the endoscope so as to make the range of the locus to be in the appropriate range in the display image.

According to the control of the abrasion B mode of the medical system 200 according to the present embodiment, the endoscope 2 is automatically operated to alternately provide the visual field in the proximity of the lesion portion and the visual field in the overhead view to the operator in according to the range of the region where the treatment is currently performed. The repetitive operations of the endoscope 2 suitable for the abrasion treatment can be automated.

According to the medical system 200 according to the present embodiment, the adjustment of the visual filed is performed according to the locus of the treatment tool 1 acquired by the predetermined period so as to prevent the visual field from frequently moving in the display image. Also, the medical system 200 performs the adjustment of the visual field according to the locus of the treatment tool 1 in the predetermined period such that the most suitable visual field showing the whole region where the treatment is currently performed rather than the current position of the treatment tool 1 can be provided.

Third Embodiment

A third embodiment of the present will be described by referring to FIG. 10A, FIG. 10B, and FIG. 11. In the present embodiment, the embodiment of determining the automatic operation of the endoscope 2 is different from that according to the first embodiment and the second embodiment. In the following description, the common configurations which are already described will be assigned with same reference signs and the reductant descriptions will be omitted.

An overall configuration of a medical system 300 according to the present embodiment is same with that of the medical system 100 according to the first embodiment. Comparing with the medical system 100, the medical system 300 is different in that the control unit 33 has an operation mode as suture mode instead of the abrasion A mode. Hereinafter, the control flow of the control unit 33 during the suture mode will be described by referring to FIG. 10A, FIG. 1.0B, and FIG. 11. FIG. 1.0A and FIG. 1.0B are captured images by the endoscope 2 of the medical system 300. FIG. 11 is a flow chart showing a control flow of the control unit 33 in the suture mode.

Figure 11:
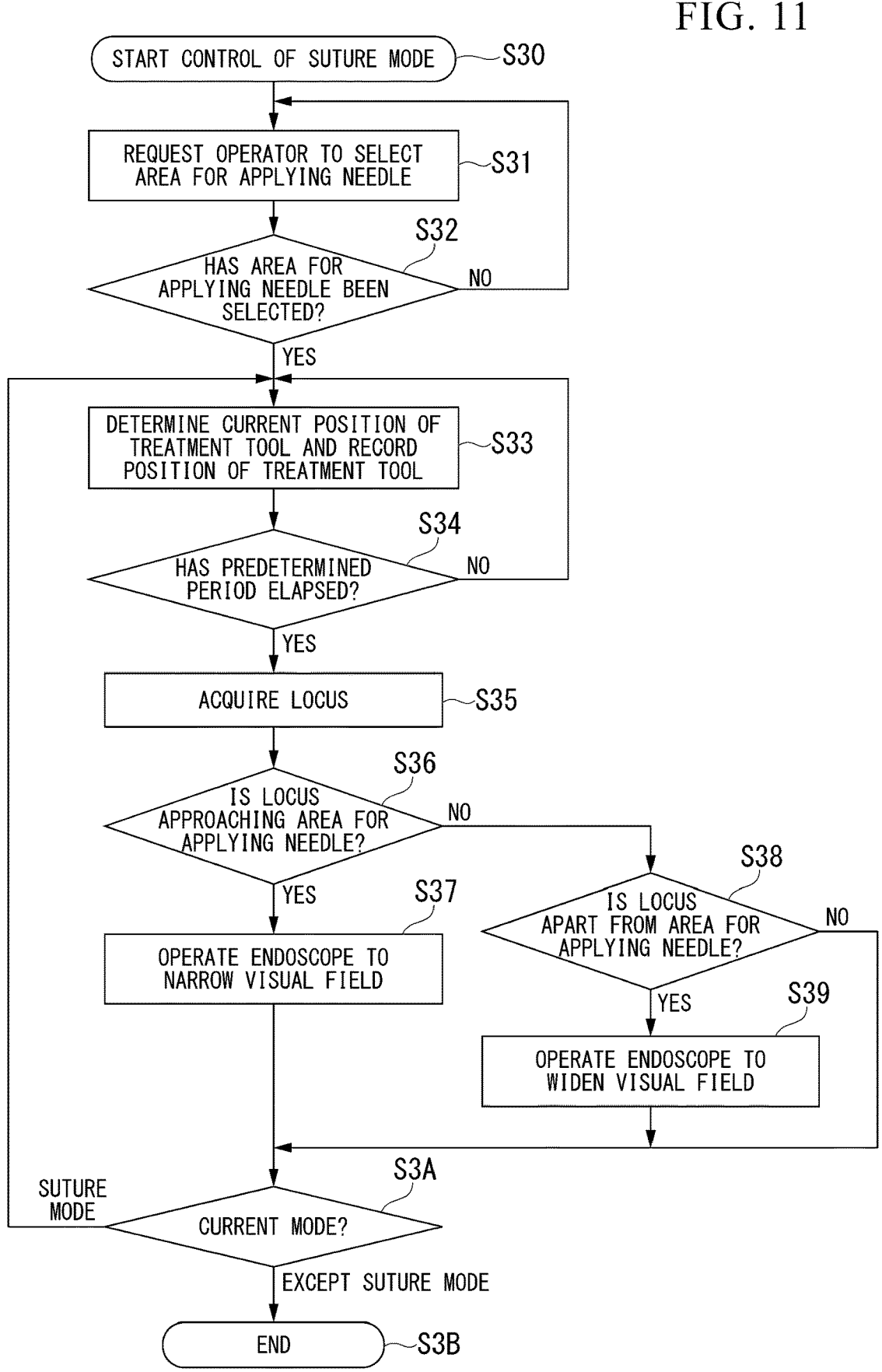
FIG. 11 is a flow chart showing a control flow of the control unit of the medical system in a suture mode.

As shown in FIG. 11, when the operation mode of the control unit 33 is changed to the suture mode, the control unit 33 starts the control of the suture mode (Step S30). Subsequently, the control unit 33 proceeds to Step S31.

In Step S31, as shown in FIG. 11, the control unit 33 requests the operator to select a region for performing the suture treatment, that is, to select a needle-applying region. A. The control unit 33 controls to display a message of requesting a selectin of the needle-applying region A on the display image on the display 4 due to the function of the image-processing unit 32.

The selection of the needle-applying region A can be realized in various methods. For example, the needle-applying region A is selected by moving the treatment portion 12 of the treatment tool 1 to the needle-applying region A and make the control unit 33 to determine the position of the treatment portion 12 after the movement. Also, in the situation in which the function of touch panel is provided in the display 4, the needle-applying region A in the display image is selected by the operator touching a part of the touch panel of the display 4. The dotted lines in FIG. 10A and FIG. 10B show the needle-applying region A set by the operator.

Subsequently, the control unit 33 proceeds to Step S32.

In Step S32, as shown in FIG. 11, the control unit determines whether the needle-applying region A is set by the operator. In the situation in which the needle-applying region A is set, the control unit 33 proceeds to Step S33 subsequently. In the situation in which the needle-applying region A is not set, the control unit 33 executes Step S31 again and be in standby for the operator to set the needle-applying region A.

Before Step S33 is executed, the control unit 33 deactivates the operation input of the operation input unit 51. Accordingly, the scopist cannot operate the joints 23 of: the arm 21 of the endoscope 2 by operating the operation input unit 51. Also, the control unit 33 activates the timer for measuring time and starts the count for the elapsed time.

In Step S33, as shown in FIG. 11, the control unit 33 determines the current position of the treatment tool 1 from the display image. The control unit 33 performs the same processing (detection processing) with that in Step S11 according to the first embodiment. Subsequently, the control unit 33 proceeds to Step S34.

In Step S34, the control unit 33 performs the same processing with that in Step S12, according to the first embodiment. In the situation in which the elapsed time exceeds the predetermined period, the control unit 33 proceeds to Step S35 subsequently. In the situation in which the elapsed time does not exceed the predetermined period, the control unit proceeds to Step S33 subsequently.

In Step S35, as shown in FIG. 11, the control unit 33 acquires the locus of the treatment tool 1. Subsequently, the control unit 33 proceeds to Step S36.

In Step S36, as shown in FIG. 11, the control unit 33 determines whether the locus of the treatment tool 1 acquired in Step S35 is near to the needle-applying region A. Since the locus of the treatment tool 1 acquired in the predetermined period is used for the determination, it is possible for the control unit 33 to determine whether the treatment tool 1 is near to the needle-applying region A.

In the situation in which the locus of the treatment tool 1 is near to the needle-applying region A, the control unit 33 proceeds to Step S37 subsequently. In the situation in which the locus of the treatment tool 1 is not near to the needle-applying region A, the control unit 33 proceeds to Step S38 subsequently.

Figure 10A:
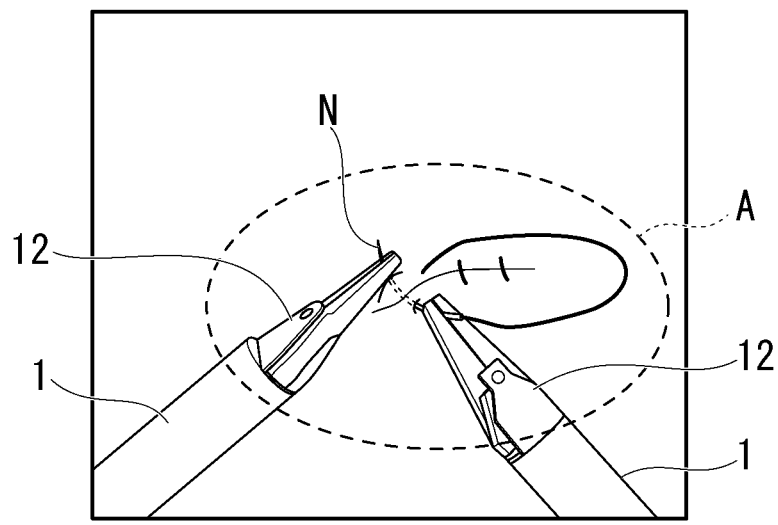
FIG. 10A is a captured image by an endoscope of a medical system according to a third embodiment of the present invention.

In Step S37, as shown in FIG. 11, the control unit 33 operates the joints 23 of the arm 21 of the endoscope 2 to operate the endoscope 2 so as to adjust the visual field of the endoscope 2 to be the visual field including the needle-applying region A and in the proximity of the lesion portion as shown in FIG. 10A (operation processing).

In the situation in which the locus of the treatment tool 1 is near to the needle-applying region A, the possibility of applying the needle to the lesion portion is high.

In Step S38, as shown in FIG. 11, the control unit 33 determines whether the locus of the treatment tool 1 acquired in Step S35 is far from the needle-applying region A. Since the locus of the treatment tool 1 acquired in the predetermined period is used for the determination, it is possible for the control unit 33 to determine whether the treatment tool 1 is far from the needle-applying region A.

In the situation in which the locus of the treatment tool 1 is far from the needle-applying region A, the control unit 33 proceeds to Step S39 subsequently. In the situation in which the locus of the treatment tool 1 is not far from the needle-applying region A, the control unit 33 proceeds to Step S3A subsequently.

Figure 10B:
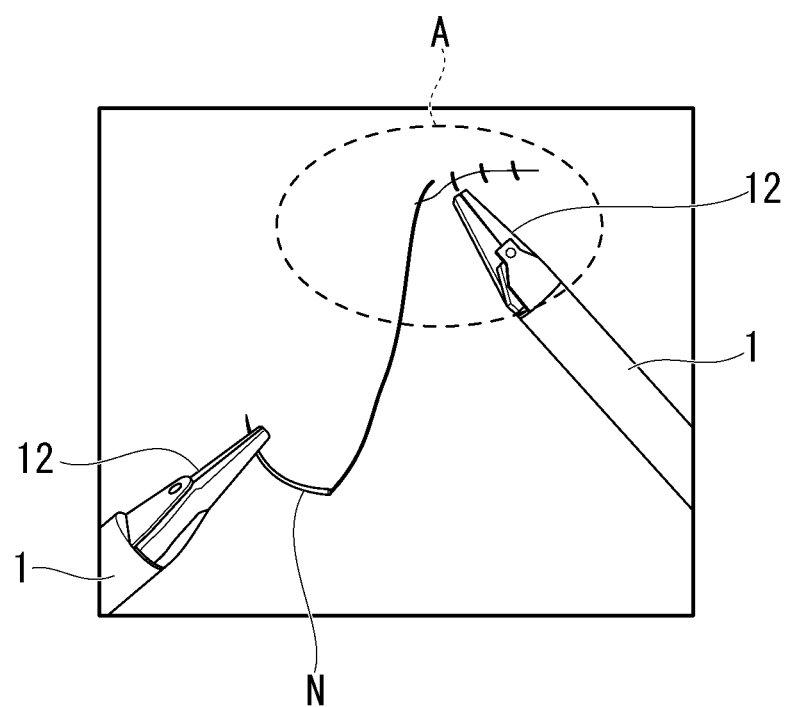
FIG. 10B is a captured image by the endoscope of the medical system according to the third embodiment.

In Step S39, as shown in FIG. 11, the control unit 33 operates the joints 23 of the arm 21 of the endoscope 2 to operate the endoscope 2 so as to adjust the visual field of the endoscope 2 to include the needle-applying region A and be the overhead view of the lesion portion as shown in FIG. 10B (operation processing). The visual field of the endoscope 2 is adjusted to include the locus of the treatment tool 1.

In the situation in which the locus of the treatment tool 1 is far from the needle-applying region A, it is considered that the needle N applied on the lesion portion is currently pulled.

In Step S3A, as shown in FIG. 11, the control unit 33 determines whether the operation mode selected by the mode-selection unit 52 is the suture mode. In the situation in which the selected operation mode is the suture mode, the control unit 33 proceeds to Step S33. In the situation in which the processing branches in Step S33, the control unit 33 resets the timer for measuring time and returns the elapsed time to zero.

In the situation in which the selected operation mode is not the suture mode, the control unit 33 proceeds to Step S3B and terminate the control of the suture mode.

The scopist operates the mode-selection unit 52 to change the operation mode of the control unit 33 to the manual mode such that the control of the suture mode by the control unit 33 is terminated and the joints 23 of the arm 21 of the endoscope can be directly operated by the operation of the operation input unit 51.

By operating the medical system 300 in such manner, the problems shown below are solved.

In the case in which the operator actually performs the suture treatment with respect to the target lesion portion, the operation of applying the needle to the lesion portion and pulling the needle N are alternately performed. In the situation of applying the needle to the lesion portion, the operator desires the visual field of the endoscope in the proximity with respect to the lesion portion. On the other hand, in the situation of pulling the needle N, generally the operator desires the visual field of the endoscope 2 to include the lesion portion in the overhead view.

Accordingly, in the suture treatment, it is necessary to alternately provide the visual filed in the proximity of the lesion portion and the visual field in the overhead view to the operator.

According to whether the treatment tool 1 is near to the needle-applying region A or far from the needle-applying region A, the control unit 33 controls the driver 31 to operate the endoscope so as to automatically adjust the visual field of the endoscope 2 to be the most suitable visual field for the suture treatment.

Effects of Third Embodiment

According to the medical system 300 according to the present embodiment, the visual field is adjusted according to the locus of the treatment tool 1 acquired per each predetermined period such that it is possible for the control unit 33 to determine whether the treatment tool 1 is near to the needle-applying region A or far from the needle-applying region A.

According to the control of the suture mode of the medical system 300 according to the present embodiment, the endoscope 2 is automatically operated to alternately provide the visual filed in the proximity of the lesion portion and the visual field including the lesion portion in the overhead view according to whether the treatment tool 1 is near to the needle-applying region A or far from the needle-applying region A. The repetitive operations of the endoscope 2 suitable for the suture treatment can be automated.

Fourth Embodiment

A fourth embodiment of the present will be described by referring to FIG. 12A, FIG. 12B, and FIG. 13. In the present embodiment, the embodiment of determining the automatic operation of the endoscope 2 is different from that according to the first embodiment to the third embodiment. In the following description, the common configurations which are already described will be assigned with same reference signs and the reductant descriptions will be omitted.

An overall configuration of a medical system 400 according to the present embodiment is same with that of the medical system 100 according to the first embodiment. Comparing with the medical system 100, the medical system 400 is different in that the control unit 33 has an operation mode as dissection mode instead of the abrasion A mode. Also, the endoscope 2 of: the medical system 400 is preferred to have an active-bending in the insertion portion 20. Hereinafter, the control flow of the control unit 33 during the dissection mode will be described by referring to FIG. 12A, FIG. 12B, and FIG. 13. FIG. 12A and FIG. 12B are captured images by the endoscope 2 of the medical system 400. FIG. 13 is a flow chart showing a control flow of the control unit 33 in the dissection mode.

Figure 13:
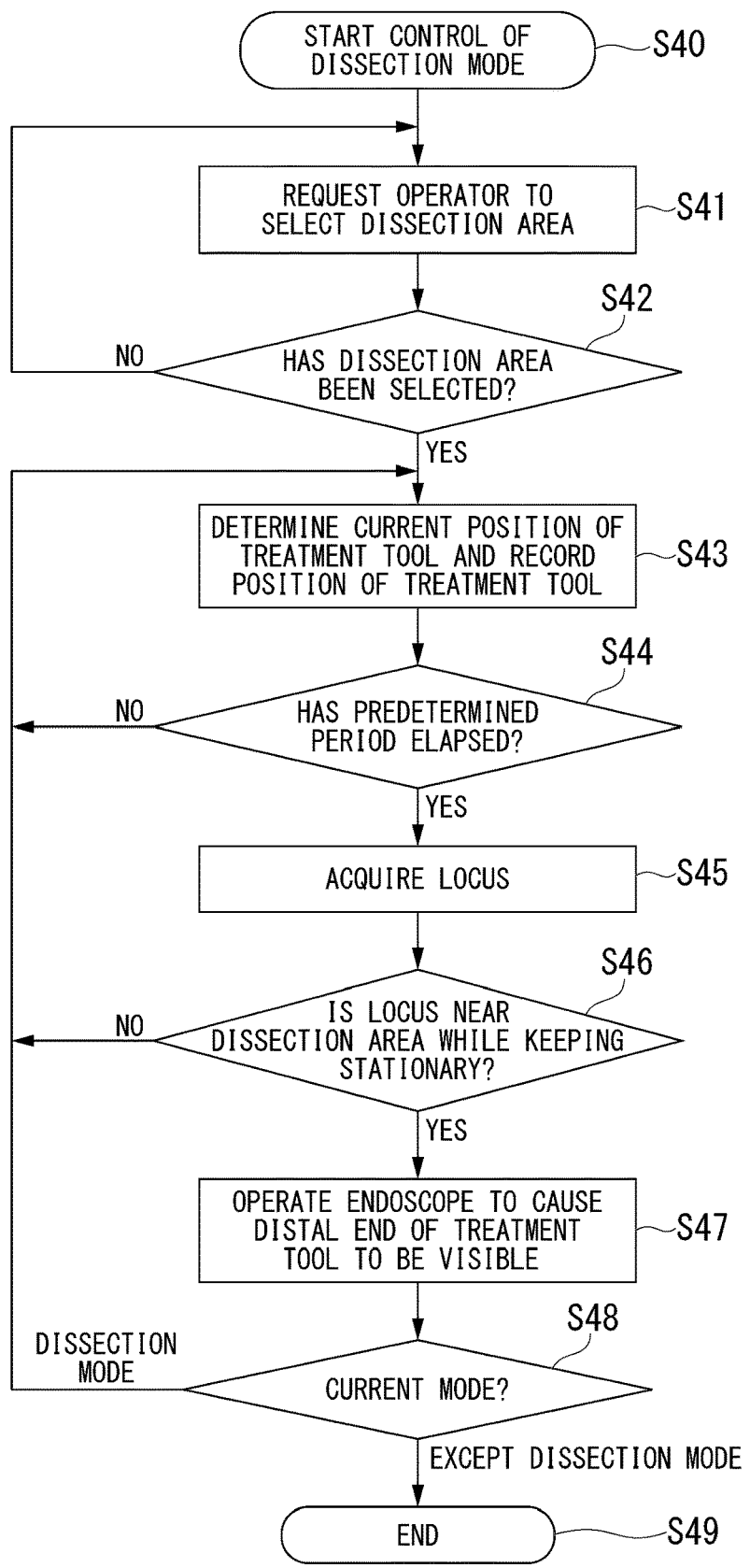
FIG. 13 is a flow chart showing a control flow of: the control unit of the medical system in a dissection mode.

As shown in FIG. 13, when the operation mode of the control unit 33 is changed to the dissection mode, the control unit 33 starts the control of the dissection mode (Step S40). Subsequently, the control unit 33 proceeds to Step S41.

In Step S41, as shown in FIG. 13, the control unit 33 requests the operator to select a region for performing the dissection treatment, that is, to select a dissection region. The control unit 33 controls to display a message of requesting a selectin of the dissection region on the display image on the display 4 due to the function of the image-processing unit 32.

The selection of the dissection region can be realized due to the same method with the selection of the needle-applying region A shown in Step S31 according to the third embodiment.

Figure 12A:
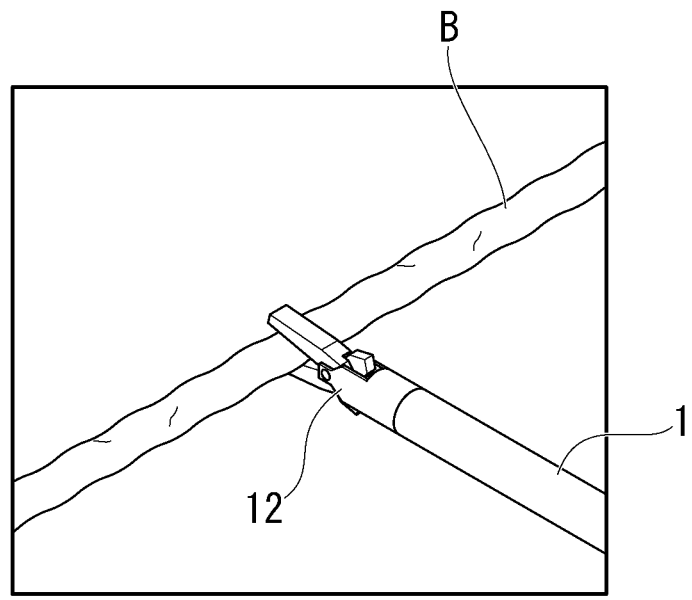
FIG. 12A is a captured image by an endoscope of a medical system according to a fourth embodiment of the present invention.
Figure 12B:
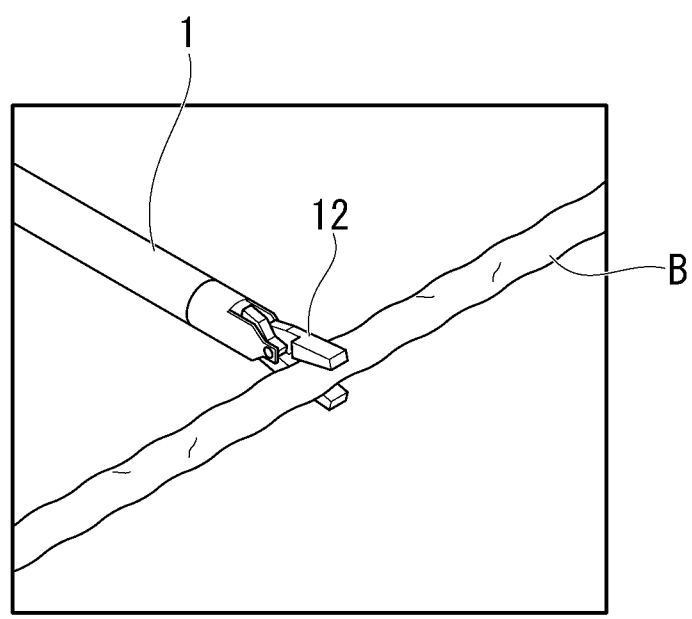
FIG. 12B is a captured image by the endoscope of the medical system according to the fourth embodiment.

For example, it is also possible to assist the selection of the dissection region by extracting the dissection region such as blood vessels B shown in FIG. 12A and FIG. 12B from the captured image of the endoscope and prompting the dissection region to the operator.

In Step S42, as shown in FIG. 13, the control unit determines whether the dissection region is determined by the operator. In the situation in which the dissection region is determined, the control unit 33 proceeds to Step S43 subsequently. In the situation in which the dissection region is not determined, the control unit 33 executes Step S41 again to be in standby for the operator to determine the dissection region.

Before Step S33 is executed, the control unit 33 deactivates the operation input of the operation input unit 51. Accordingly, the scopist cannot operate the joints 23 of the arm 21 of the endoscope 2 by operating the operation input unit 51. Also, the control unit 33 activates the timer for measuring time and starts the count for the elapsed time.

In Step S43, as shown in FIG. 13, the control unit 33 determines the current position of the treatment tool 1 from the display image. The control unit 33 performs the same processing (detection processing) with that in Step S11 according to the first embodiment. Subsequently, the control unit 33 proceeds to Step S44.

In Step S44, the control unit 33 performs the same processing with that in Step S12, according to the first embodiment. In the situation in which the elapsed time exceeds the predetermined period, the control unit 33 proceeds to Step S45 subsequently. In the situation in which the elapsed time does not exceed the predetermined period, the control unit proceeds to Step S43 subsequently.

In Step S45, as shown in FIG. 13, the control unit 33 acquires the locus of the treatment tool 1. Subsequently, the control unit 33 proceeds to Step S46.

In Step S46, as shown in FIG. 13, the control unit 33 determines whether the treatment tool 1 is near to the dissection region and stationary according to the locus of the treatment tool 1 acquired in Step S45 as shown in FIG. 12A. Since the locus of the treatment tool 1 acquired in the predetermined period is used for the determination, it is possible for the control unit 33 to determine whether the treatment tool 1 is near to the dissection region and stationary.

In the situation in which the treatment tool 1 is near to the dissection region and stationary, the control unit 33 proceeds to Step S47 subsequently. Otherwise, the control unit 33 proceeds to Step S48 subsequently.

In Step S47, as shown in FIG. 13, the control unit 33 operates the joints 23 of the arm 21 of the endoscope 2 to operate the endoscope 2 so as to adjust the visual field of the endoscope 2 such that the distal end of the treatment tool is captured and imaged (operation processing).

In the situation in which the treatment tool 1 is near to the dissection region, the possibility of starting the dissection treatment with respect to the dissection region is high.

The method of adjusting the visual field so as to make the distal end of the treatment tool to be captured can be realized by various methods. For example, in the situation in which the image portion 22 of the endoscope 2 has the function of measuring a distance such as the stereo camera, a longitudinal axis of the insertion portion 10 of the treatment tool 1 is extracted from the stereo image as three-dimensional vector information. Subsequently, the joints 23 of the arm 21 of the endoscope 2 are operated to adjust the visual field of the endoscope 2 such that an inner product of the extracted longitudinal axis vector of the insertion portion 10 and an optical axis vector of the image portion 22 of the endoscope 2 is minus.

Subsequently, the control unit 33 proceeds to Step S48.

In Step S48, as shown in FIG. 13, the control unit 33 determines whether the operation mode selected by the mode-selection unit 52 is the dissection mode. In the situation in which the selected operation mode is the dissection mode, the control unit 33 proceeds to Step S43. In the situation in which the processing branches in Step S43, the control unit 33 resets the timer for measuring time and returns the elapsed time to zero.

In the situation in which the selected operation mode is not the dissection mode, the control unit 33 proceeds to Step S48 and terminate the control of the dissection mode.

Here, even if the selected operation mode is the dissection mode, the operation mode may be forcibly changed to the manual mode. It is to prevent the endoscope 2 from being automatically operated during the actual dissection processing.

The scopist operates the mode-selection unit 52 to change the operation mode of the control unit 33 to the manual mode such that the control of the dissection mode by the control unit 33 is terminated and the joints 23 of the arm 21 of the endoscope 2 can be directly operated by the operation of the operation input unit 51.

By operating the medical system 400 in such manner, the problems shown below are solved.

In the case in which the operator actually performs the dissection treatment with respect to the target lesion portion, before the treatment tool 1 is disposed, the operator desires the visual field so as to see both the lesion portion and the treatment tool 1 in order to dispose the treatment tool 1 at the appropriate position. On the other hand, after the treatment tool is disposed, the operator desires the visual field so as to capture the distal end of the treatment tool 1 in order to observe the actually dissected portion.

Accordingly, during the dissection treatment, since the visual fields desired by the operator before disposing the treatment tool 1 and after disposing the treatment tool 1 are different, in some case, after the treatment tool 1 is disposed, it is necessary to provide a different visual field from the visual filed provided before the treatment tool 1 is disposed to the operator.

In the situation in which the treatment tool 1 is near to the dissection region and stationary, it is determined that the treatment tool 1 has been disposed and the visual field of the endoscope 2 is automatically adjusted to be the most suitable visual field for the dissection treatment by the control unit 33 controlling the driver to operate the endoscope 2.

Effects of Fourth Embodiment

According to the medical system 400 according to the present embodiment, the visual field is adjusted according to the locus of the treatment tool 1 acquired per each predetermined period such that it is possible for the control unit 33 to determine whether the treatment tool 1 is near to the dissection region and stationary.

According to the control of the dissection mode of the medical system 400 according to the present embodiment, the endoscope 2 is automatically operated such that the distal end of the treatment tool 1 is captured according to that the treatment tool 1 is near to the dissection region and stationary. During the dissection mode, the repetitive operations of the endoscope 2 suitable for the dissection treatment can be automated.

Fifth Embodiment

A fifth embodiment of the present will be described by referring to FIG. 14. In the present embodiment, a number of variations of the operation modes is different from that according to the first embodiment to the fourth embodiment. In the following description, the common configurations which are already described will be assigned with same reference signs and the reductant descriptions will be omitted.

An overall configuration of a medical system 500 according to the present embodiment is same with that of the medical system 100 according to the first embodiment. Comparing with the medical system 100, the medical system 500 is different in that the control unit 33 has a plurality of operation modes.

Figure 14:
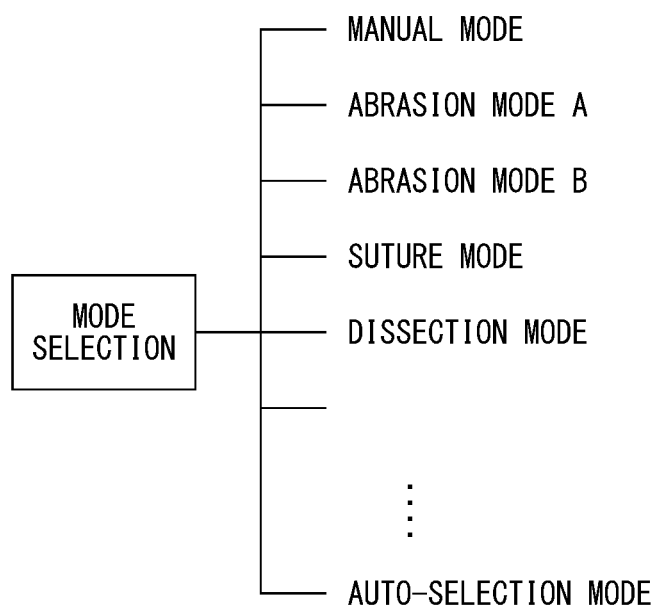
FIG. 14 is a view showing variations of operation modes of a medical system according to a fifth embodiment of the present invention.

FIG. 14 is a view showing operation modes which can be controlled by the control unit 33 of the medical system 500. The control unit 33 of the medical system 500 can be operated under the manual mode, the abrasion A mode included by the control unit 33 of the medical system 100, the abrasion B mode included by the control unit 33 of the medical system 200, the suture mode included by the control unit 33 of the medical system 300, and the dissection mode included by the control unit 33 of the medical system 400.

The control unit 33 of the medical system 500 may be configured to be operable only under a part of the operation modes indicated above.

The operator or the scopist operates the mode-selection unit 52 to change the operation mode of the control unit 33 to a suitable one for the treatment. The operator or the scopist can achieve the most suitable visual field for different treatment by using the different operation modes.

The control unit 33 of the medical system 500 may have an "automatic-selection mode" as one of the plurality of operation modes. In the automatic-selection mode, the control unit 33 automatically selects the operation mode of the endoscope 2 according to a selection rule of the endoscope 2 which is acquired by a machine learning in advance.

The selection rule in the automatic-selection mode is a function when the display image is an input and the operation mode is an output. Pairs of the selections made by the scopist with respect to the mode-selection unit 52 in the manual mode and the corresponding display images are the learning data. The function can be achieved by using the method such as the neural network and the like according to the appropriate amount of the learning data.

The selection rule can be achieved by using the learning data acquired during the surgery by a specific operator. By achieving the specific selection rule for the specific operator, the medical system 500 can provide the automatic adjustment of the visual field for the specific operator.

In the automatic-selection mode, the medical system 500 automatically is configured to operate the endoscope 2 using the operation rule achieved according to the learning data acquired based on the actual display image and the operations to the mode-selection unit 52. According to the automatic-selection mode, it is not necessary for the operator or the scopist to select the operation mode due to the variation of the treatment.

Effects of Fifth Embodiment

According to the medical system 500 according to the present embodiment, the operation mode suitable for the treatment can be selected from the plurality of operable operation modes, and the repetitive operations of the endoscope 2 suitable for each treatment can be automated.

According to the medical system 500 according to the present embodiment, by applying the automatic-selection mode, it is not necessary to select the operation mode due to the variation of the treatment.

Although preferred embodiments of the present invention have been described above, the present invention is not limited to the embodiments and modifications thereof. Additions, omissions, substitutions and other changes in the structure are possible without departing from the spirit of the present invention. The present invention is not limited by the foregoing description but is limited only by the scope of the appended claims.

What is claimed is:

1. A medical system, comprising:
an endoscope comprising an image sensor configured to capture an image; and
a processor configured to:
    determine a plurality of positions of a treatment tool captured in a plurality of images by the image sensor over a predetermined time period;
    determine an area defined by the plurality of positions of the treatment tool; and
    control a driver for operating the endoscope to move the area defined by the plurality of positions of the treatment tool to a predetermined region in a next image captured by the image sensor.

2. The medical system according to claim 1,
wherein the processor is configured to:
    determine a center of the area defined by the plurality of positions of the treatment tool by calculating an average coordinate or a centroid of the plurality of positions of the treatment tool; and
    in controlling the driver to move the endoscope, control the driver to move the area defined by the plurality of positions of the treatment tool to the predetermined region in the next image to make the center of the area defined by the plurality of positions of the treatment tool to be at a center of the next image.

3. The medical system according to claim 2,
wherein the treatment tool is a first treatment tool,
wherein the predetermined region is a first predetermined region, and
wherein the processor is configured to:
    determine a plurality of positions of a second treatment tool captured in the plurality of images by the image sensor over the predetermined time period;
    determine an area defined by the plurality of positions of the second treatment tool;
    determine a center of the area defined by the plurality of positions of the first treatment tool and a center of the area defined by the plurality of positions of the second treatment tool; and
    determine a center of the next image to be acquired according to the center of the area defined by the plurality of positions of the first treatment tool and the center of the area defined by the plurality of positions of the second treatment tool.

4. The medical system according to claim 3,
wherein the processor is configured to:
- calculate average coordinates of the center of the area defined by the plurality of positions of the first treatment tool;
- calculate average coordinates of the center of the area defined by the plurality of positions of the second treatment tool; and
- determine the center of the next image to be acquired according to the average coordinates of the center of the area defined by the plurality of positions of the first treatment tool and the average coordinates of the center of the area defined by the plurality of positions of the second treatment tool.

5. The medical system according to claim 1,
wherein the processor is configured to:
- determine a range of the area defined by the plurality of positions of the treatment tool; and
- in controlling the driver to move the endoscope, control the driver to move the endoscope to make the range of the area defined by the plurality of positions of the treatment tool to be in a predetermined range, as the predetermined region, of the next image.

6. The medical system according to claim 1,
wherein the processor is configured to:
- request an operator to select a partial region in an initial image;
- determine whether the area defined by the plurality of positions of the treatment tool is within a predetermined distance from the partial region selected; and
- in controlling the driver to move the endoscope,
  - control the driver to move the endoscope to move the area defined by the plurality of positions of the treatment tool to the predetermined region in the next image to make a visual field of the next image to be focused on the partial region in a situation in which the area defined by the plurality of positions of the treatment tool is within the predetermined distance from the partial region selected; and
  - control the driver to move the endoscope move the area defined by the plurality of positions of the treatment tool to the predetermined region in the next image to make the visual field of the next image to be an overhead view of the partial region in a situation in which the area defined by the plurality of positions of the treatment tool is not within the predetermined distance from the partial region selected.

7. The medical system according to claim 1,
wherein the processor is configured to:
- request an operator to select a partial region in an initial image;
- determine whether the area defined by the plurality of positions of the treatment tool is within a predetermined distance from the partial region selected;
- determine whether the treatment tool is stationary; and
- in controlling the driver to move the endoscope, control the driver to move the endoscope to move the area defined by the plurality of positions of the treatment tool to the predetermined region in the next image so as to capture a distal end of the treatment tool in the next image in a situation in which the area defined by the plurality of positions of the treatment tool is within the predetermined distance from the partial region selected and the treatment tool is determined to be stationary.

8. The medical system according to claim 1,
wherein the processor is configured to selectively switch between operating under operable operation modes comprising:
- an abrasion A mode in which the processor is configured to:
  - determine a center of the area defined by the plurality of positions of the treatment tool by calculating an average coordinate or a centroid of the plurality of positions of the treatment tool; and
  - in controlling the driver to move the endoscope, control the driver to move the area defined by the plurality of positions of the treatment tool to the predetermined region in the next image to make the center of the area defined by the plurality of positions of the treatment tool to be at a center of the next image;
- an abrasion B mode in which the processor is configured to:
  - determine a range of the area defined by the plurality of positions of the treatment tool; and
  - in controlling the driver to move the endoscope, control the driver to move the endoscope to make the range of the area defined by the plurality of positions of the treatment tool to be in a predetermined range, as the predetermined region, of the next image;
- a suture mode in which the processor is configured to:
  - request an operator to select a partial region in an initial image;
  - determine whether the area defined by the plurality of positions of the treatment tool is within a predetermined distance from the partial region selected; and
  - in controlling the driver to move the endoscope,
    - control the driver to move the endoscope to move the area defined by the plurality of positions of the treatment tool to the predetermined region in the next image to make a visual field of the next image to be focused on the partial region in a situation in which the area defined by the plurality of positions of the treatment tool is within the predetermined distance from the partial region selected; and
    - control the driver to move the endoscope to move the area defined by the plurality of positions of the treatment tool to the predetermined region in the next image to make the visual field of the next image to be an overhead view of the partial region in a situation in which the area defined by the plurality of positions of the treatment tool is not within the predetermined distance from the partial region selected;
- a dissection mode in which the processor is configured to:
  - request an operator to select a partial region in an initial image;
  - determine whether the area defined by the plurality of positions of the treatment tool is within a predetermined distance from the partial region selected;
  - determine whether the treatment tool is stationary; and in controlling the driver to move the endoscope, control the driver to move the endoscope to move the area defined by the plurality of positions of the treatment tool to the predetermined region in the next image so as to capture a distal end of the treatment tool in the next image in a situation in which the area defined by the plurality of positions of the treatment tool is within the predetermined distance from the partial region selected and the treatment tool is determined to be stationary.

9. An operation method of a medical system having, an endoscope having an image sensor configured to capture an image, comprising:
   determining a plurality of positions of a treatment tool captured in a plurality of images by the image sensor over a predetermined time period;
   determining an area defined by the plurality of positions of the treatment tool; and
   controlling a driver for operating the endoscope to move the area defined by the plurality of positions of the treatment tool to a predetermined region in a next image captured by the image sensor.

10. The operation method according to claim 9, comprising:
    determining a center of the area defined by the plurality of positions of the treatment tool by calculating an average coordinate or a centroid of the plurality of positions of the treatment tool; and
    in controlling the driver to move the endoscope, controlling the driver to move the area defined by the plurality of positions of the treatment tool to the predetermined region in the next image to make the center of the area defined by the plurality of positions of the treatment tool to be at a center of the next image.

11. The operation method according to claim 10,
    wherein the treatment tool is a first treatment tool,
    wherein the predetermined region is a first predetermined region, and
    wherein the operation method comprises:
       determining a plurality of positions of a second treatment tool captured in the plurality of images by the image sensor over the predetermined time period;
       determining an area defined by the plurality of positions of the second treatment tool;
       determining a center of the area defined by the plurality of positions of the first treatment tool and a center of the area defined by the plurality of positions of the second treatment tool; and
       determining a center of the next image to be acquired according to the center of the area defined by the plurality of positions of the first treatment tool and the center of the area defined by the plurality of positions of the second treatment tool.

12. The operation method according to claim 11, comprising:
    calculating average coordinates of the center of the area defined by the plurality of positions of the first treatment tool;
    calculating average coordinates of the center of the area defined by the plurality of positions of the second treatment tool; and
    determining the center of the next image to be acquired according to the average coordinates of the center of the area defined by the plurality of positions of the first treatment tool and the average coordinates of the center of the area defined by the plurality of positions of the second treatment tool.

13. The operation method of a medical system according to claim 9, comprising:
    determining a range of the area defined by the plurality of positions of the treatment tool; and
    in controlling the driver to move the endoscope, controlling the driver to move the endoscope to make the range of the area defined by the plurality of positions of the treatment tool to be in a predetermined range, as the predetermined region, of the next image.

14. The operation method of a medical system according to claim 9, comprising:
    requesting an operator to select a partial region in an initial image;
    determining whether the area defined by the plurality of positions of the treatment tool is within a predetermined distance from the partial region selected; and
    in controlling the driver to move the endoscope,
       controlling the driver to move the endoscope to move the area defined by the plurality of positions of the treatment tool to the predetermined region in the next image to make a visual field of the next image to be focused on the partial region in a situation in which the area defined by the plurality of positions of the treatment tool is within the predetermined distance from the partial region selected; and
       controlling the driver to move the endoscope to move the area defined by the plurality of positions of the treatment tool to the predetermined region in the next image to make the visual field of the next image to be an overhead view of the partial region in a situation in which the area defined by the plurality of positions of the treatment tool is not within the predetermined distance from the partial region selected.

15. The operation method of a medical system according to claim 9, comprising:
    requesting an operator to select a partial region in an initial image;
    determining whether the area defined by the plurality of positions of the treatment tool is within a predetermined distance from the partial region selected;
    determining whether the treatment tool is stationary; and
    in controlling the driver to move the endoscope, controlling the driver to move the endoscope to move the area defined by the plurality of positions of the treatment tool to the predetermined region in the next image so as to capture a distal end of the treatment tool in the next image in a situation in which the area defined by the plurality of positions of the treatment tool is within the predetermined distance from the partial region selected and the treatment tool is determined to be stationary.

16. The operation method according to claim 9, comprising:
    selectively switching between operating under operable operation modes comprising:
       an abrasion A mode comprising:
          determining a center of the area defined by the plurality of positions of the treatment tool by calculating an average coordinate or a centroid of the plurality of positions of the treatment tool; and
          in controlling the driver to move the endoscope, controlling the driver to move the area defined by the plurality of positions of the treatment tool to the predetermined region in the next image to make the center of the area defined by the plurality of positions of the treatment tool to be at a center of the next image;

an abrasion B mode comprising:
  determining a range of the area defined by the plurality of positions of the treatment tool; and
  in controlling the driver to move the endoscope, controlling the driver to move the endoscope to make the range of the area defined by the plurality of positions of the treatment tool to be in a predetermined range, as the predetermined region, of the next image;
a suture mode comprising:
  requesting an operator to select a partial region in an initial image;
  determining whether the area defined by the plurality of positions of the treatment tool is within a predetermined distance from the partial region selected; and
  in controlling the driver to move the endoscope,
    controlling the driver to move the endoscope to move the area defined by the plurality of positions of the treatment tool to the predetermined region in the next image to make a visual field of the next image to be focused on the partial region in a situation in which the area defined by the plurality of positions of the treatment tool is within the predetermined distance from the partial region selected; and
    controlling the driver to move the endoscope to move the area defined by the plurality of positions of the treatment tool to the predetermined region in the next image to make the visual field of the next image to be an overhead view of the partial region in a situation in which the area defined by the plurality of positions of the treatment tool is not within the predetermined distance from the partial region selected;
a dissection mode comprising:
  requesting an operator to select a partial region in an initial image;
  determining whether the area defined by the plurality of positions of the treatment tool is within a predetermined distance from the partial region selected;
  determining whether the treatment tool is stationary; and
  in controlling the driver to move the endoscope, controlling the driver to move the endoscope to move the area defined by the plurality of positions of the treatment tool to the predetermined region in the next image so as to capture a distal end of the treatment tool in the next image in a situation in which the area defined by the plurality of positions of the treatment tool is within the predetermined distance from the partial region selected and the treatment tool is determined to be stationary.

\* \* \* \* \*